United States Patent [19]

Palladino et al.

[11] Patent Number: 5,767,071

[45] Date of Patent: Jun. 16, 1998

[54] SEVENMER CYCLIC PEPTIDE INHIBITORS OF DISEASES INVOLVING $\alpha_v\beta_3$

[75] Inventors: Michael A. Palladino, Olivenhain; Bruce A. Lee, San Diego; William D. Huse, Del Mar; Judith A. Varner, Encinitas, all of Calif.

[73] Assignee: IXSYS Incorporated, San Diego, Calif.

[21] Appl. No.: 482,106

[22] Filed: Jun. 7, 1995

[51] Int. Cl.$^6$ .......................... A61K 38/12; A61K 38/00; C07K 7/00; C07K 7/50

[52] U.S. Cl. ........................... 514/11; 514/15; 530/317; 530/328

[58] Field of Search ................... 514/11, 15; 530/328, 530/317

[56] References Cited

U.S. PATENT DOCUMENTS

| | | | |
|---|---|---|---|
| 4,271,068 | 6/1981 | Kamber et al. | 260/112.5 |
| 4,792,525 | 12/1988 | Ruoslahti et al. | 435/240.243 |
| 4,988,621 | 1/1991 | Ruoslahti et al. | 435/240.2 |
| 5,262,520 | 11/1993 | Plow et al. | 530/326 |

FOREIGN PATENT DOCUMENTS

| | | |
|---|---|---|
| 0 576 898 A3 | 1/1994 | European Pat. Off. |
| 0 578 083 A3 | 1/1994 | European Pat. Off. |
| WO 95/14714 | 6/1995 | WIPO |

OTHER PUBLICATIONS

STN search results

Brooks et al., "Requirement of Vascular Integrin $\alpha_v\beta_3$ for Angiogenesis" *Science*, vol. 264, pp. 569–571 (1994).

Brooks et al., "Integrin $\alpha_v\beta_3$ Antagonists Promote Tumor Regression by Inducing Apoptosis of Angiogenic Blood Vessels" *Cell*, vol. 79, pp. 1157–1164 (1994).

Nicosia and Bonanno, "Inhibition of Angiogenesis In Vitro by Arg–Gly–Asp–Containing Synthetic Peptide" *Amer. J. Path.*, vol. 138, pp. 829–833.

Choi et al., "Inhibition of Neointimal Hyperplasia by Blocking $\alpha_v\beta_3$ Integrin with a Small Peptide Antagonist G*pen*-GRGDSPCA" *J. Vasc. Surg.*, vol. 19, pp. 125–134 (1994).

Matusno et al., "Inhibition of Integrin Function by a Cyclic RGD–Containing Peptide Prevents Neointima Formation" *Circ.* 90, pp. 2203–2206 (1994).

Miyauchi et al., "Recognition of Osteopontin and Related Peptides by an $\alpha_v\beta_3$ Integrin Stimulates Immediate Cell Signals in Osteoclasts" *J. Biol. Chem.*, vol. 266, pp. 20369–20374.

Sato et al., "Echistatin Is a Potent Inhibitor of Bone Resorption in Culture" *J. Cell. Biol.*, vol. 111, pp. 1713–1723 (1990).

Ross et al., "Interactions Between the Bone Matrix Proteins Osteopontin and Bone Sialoprotein and the Osteoclast Integrin $\alpha_v\beta_3$ Potentiate Bone Resorption" *J. Biol. Chem.*, vol. 268, pp. 9901–9907 (1993).

Horton et al., "Arg–Gly–Asp (RGD) Peptides and the Anti-Vitronectin Receptor Antibody 23C6 Inhibit Dentine Resorption and Cell Spreading by Osteoclasts" *Exp. Cell Res.*, vol. 195, pp. 368–375 (1991).

Liaw et al., "The Adhesive and Migratory Effects of Osteopontin Are Mediated via Distinct Cell Surface Integrins" *J. Clin. Invest.*, vol. 95, pp. 713–724 (1995).

Pierschbacher and Ruoslahti, "Variants of the Cell Recognition Site of Fibronectin that Retain Attachment–Promoting Activity" *Proc. Natl. Acad. Sci.*, vol. 81, pp. 5985–5988 (1984).

Ruoslahti and Pierschbacher, "Arg–Gly–Asp: A Versatile Cell Recognition Signal" *Cell*, vol. 44, pp. 517–518 (1986).

Smith et al., Interaction of Integrins $\alpha_v\beta_3$ and Glycoprotein IIb–IIIa with Fibrinogen *J. Biol. Chem.*, vol. 265, pp. 12267–12271 (1990).

Ruoslahti and Pierschbacher, "New Perspectives in Cell Adhesion: RGD and Integrins" *Science*, vol. 238, pp. 491–497 (1987).

Humphries, "The Molecular Basis and Specificity of Integrin–Ligand Interactions" *J. Cell Sci.*, vol. 97, pp. 585–592 (1990).

Ruoslahti, "Integrins" *J. Clin. Invest.*, vol. 87, pp. 1–5 (1991).

Pierschbacher and Ruoslahti, "Influence of Stereochemistry of the Sequence Arg–Gly–Asp–Xaa on Binding Specificity in Cell Adhesion" *J. Bio. Chem.*, vol. 262, pp. 17924–17928 (1987).

Aumailley et al., "Arg–Gly–Asp Constrained Within Cyclic Pentapeptides" *FEBS*, vol. 291, pp. 50–54 (1991).

Koivunen et al., "Phage Libraries Displaying Cyclic Peptides with Different Ring Sizes: Ligand Specificities of the RGD–Directed Integrins" *Biotech.*, vol. 13, pp. 265–270 (1995).

Obara et al., "Site–Directed Mutagenesis of the Cell–Binding Domain of Human Fibronectin: Separable, Synergistic Sites Mediate Adhesive Function" *Cell*, 53, pp. 649–657 (1988).

Beacham et al., "Selective Inactivation of the Arg–Gly–Asp–Ser (RGDS) Binding site in von Willebrand Factor by Site–Directed Mutagenesis" *J. Biol. Chem.*, vol. 267, pp. 3409–3415 (1992).

Cherny et al., "Site–Directed Muta–Genesis of the Arginine–Glycine–Aspartic Acid in Vitronectin Abolishes Cell Adhesion" *J. Biol. Chem.*, vol. 268, pp. 9725–9729 (1993).

(List continued on next page.)

*Primary Examiner*—Cecilia J. Tsang
*Assistant Examiner*—Michael Borin
*Attorney, Agent, or Firm*—Needle & Rosenberg, P.C.

[57] ABSTRACT

The present invention includes non-RGD, nine amino acid cyclic peptides that inhibit the function of the integrin receptor, $\alpha_v\beta_3$. These peptides display surprisingly potent antagonist activity despite the lack of the consensus binding sequence Arg-Gly-Asp, and present opportunities for selective targeting to the $\alpha_v\beta_3$ receptor. Pharmaceutical compositions and methods of use are also disclosed. The therapeutic uses for the inventive peptides include treating diseases involving $\alpha_v\beta_3$ receptors such as osteoporosis, restenosis, and angiogenic-based diseases, including cancer, arthritis, and diabetic retinopathy.

10 Claims, No Drawings

OTHER PUBLICATIONS

Cheresh, "Integrins: Structure, Function, and Biological Properties" *Advances in Molecular and Cell Biology*, vol. 6, pp. 225–252 (1993).

Luscinskas and Lawler, "Integrins as Dynamic Regulators of Vascular Function" *The FASEB Journal*, vol. 8, pp. 929–938 (1994).

Nowlin et al., "A Novel Cyclic Pentapeptide Inhibits $\alpha 4\beta 1$ and $\alpha 5\beta 1$ Integrin–Mediated Cell Adhesion" *The Journal of Biological Chemistry*, vol. 27, pp. 20352–20359 (1993).

Koivunen et al., "Selection of Peptides Binding to the $\alpha_5\beta_1$ Integrin from Phage Display Library" *The Journal of Biological Chemistry*, vol. 27, pp. 20205–20210 (1993).

Koivunen et al., "Isolation of a Highly Specific Ligand for the $\alpha_5\beta_1$ Integrin from a Phage Display Library" *The Journal of Cell Biology*, vol. 124, pp. 373–380 (1994).

Scarborough et al., "Barbourin" *The Journal of Biological Chemistry*, vol. 266, pp. 9359–9362 (1991).

McDowell and Gadek, "Structural Studies of Potent Constrained RGD Peptides" *Journal of the American Chemical Society*, vol. 114, pp. 9245–9253 (1992).

Barker et al., "Cyclic RGD Peptide Analogues as Antiplatelet Antithrombotics" *Journal of Medicinal Chemistry*, vol. 35, pp. 2040–2048 (1992).

Nip et al., (1992) "Human Melanoma Cells Derived From Lymphatic Metastases Use Integrin $\alpha_v\beta_3$ to Adhere to Lymph Node Vitronectin" *J. Clin. Invest.* 90:1406–1413.

Pfaff et al., (1994) "Selective Recognition of Cyclic RGD Peptides of NMR Defeined Conformation by $\alpha IIb\beta 3$, $\alpha V\beta 3$, and $\alpha 5\beta 1$ Integrins" *J. Biol. Chem.* 269(32):20233–20238.

Leven et al., (1992) "Extracellular Matrix Stimulation of Guinea Pig Megakaryocyte Proplatelet Formation in vitro Is Mediated Through the Vitronectin Receptor" *Exp. Hematol.* 20:1316–1322.

Horton et al., (1993) "Modulation of Vitronectin Receptor–Mediated Osteoclast Adhesion by Arg–Gly–Asp Peptide Analogs: A Structure–Function Analysis" *Journal of Bone and Mineral Research* 8(2):239–247.

SEVENMER CYCLIC PEPTIDE INHIBITORS OF DISEASES INVOLVING $\alpha_v\beta_3$

TECHNICAL FIELD

The present invention relates to compositions and methods of treating and preventing $\alpha_v\beta_3$ mediated diseases, particularly angiogenic diseases, by using certain novel $\alpha_v\beta_3$ specific peptides. These peptides are also useful for diagnosing such diseases.

BACKGROUND

The integrin receptor referred to as $\alpha_v\beta_3$ serves as a receptor for a number of extracellular matrix proteins such as vitronectin, thrombospondin, von Willebrand factor, fibrinogen, fibrin and fibrinectin, and as such, can mediate various disease states. For example, it has been implicated in diseases such as angiogenic diseases (those pathological conditions that are affected by the proliferation of new blood vessels, e.g., cancer, diabetic retinopathy, and rheumatoid arthritis), osteoporosis (reduction in bone mass), and restenosis (migration and proliferation of smooth muscle cells). Certain antibodies to $\alpha_v\beta_3$ and certain peptides containing an R-G-D (Arg-Gly-Asp) sequence have been shown to bind to $\alpha_v\beta_3$ and inhibit angiogenesis, osteoclast activity, and smooth muscle cell (SMC) migration and proliferation.

The growth of new blood vessels, or angiogenesis, involves $\alpha_v\beta_3$ and this process plays a key role in development, wound repair, and inflammation. The process also appears to contribute to pathological conditions such as diabetic retinopathy, rheumatoid arthritis, and cancer. There has been much interest in developing therapeutic agents that inhibit angiogenesis in these contexts and thus, treat disease states that are dependent on angiogenesis. Additionally, $\alpha_v\beta_3$ binding peptides may be used to identify the presence of the receptor and thus diagnose $\alpha_v\beta_3$ disease.

The role of $\alpha_v\beta_3$ in the angiogenic process has been demonstrated using antibody and peptide inhibitors of this receptor. For example, antibodies to $\alpha_v\beta_3$ blocked angiogenesis induced by basic fibroblast growth factor (bFGF), tumor necrosis factor $\alpha$ (TNF-$\alpha$) and human melanoma fragments, but had no effect on preexisting vessels. Brooks et al., Science, Vol. 264, pages 569-571 (1994). The authors of this study suggested that $\alpha_v\beta_3$ may be a useful therapeutic target for diseases characterized by neovascularization or angiogenesis.

The use of the $\alpha_v\beta_3$ receptor specific antibody, LM609, was also the subject of a Brooks et al., Cell, Vol. 79, pages 1157-1164 (1994), where the antibody was shown to inhibit angiogenesis in a chicken embryo tumor model. Intravenous administration of the antibody caused tumor growth arrest and regression. A cyclic peptide containing the sequence Arg-Gly-Asp or RGD (cyclo-RGDfv) was also shown in this Cell publication to inhibit the neovascularization process in the chicken tumor model. These results support the earlier findings of Nicosia and Bonanno, Amer. J. Path., Vol. 138, pages 829-833 (1991), who showed in 1991 that the synthetic peptide (SEQ ID:18) Gly-Arg-Gly-Asp-Ser (GRGDS) inhibits angiogenesis in vitro.

In addition to angiogenesis, the $\alpha_v\beta_3$ integrin has been demonstrated to play a role in smooth muscle cell migration. This has been shown using antagonists of the $\alpha_v\beta_3$ receptor including the LM609 antibody, and peptides (SEQ ID:1) GpenGRGDSPCA and N-mercapto acetyl D-Tyr-Arg-Gly-Asp-sulfide (Choi et al., J. Vasc. Surg., Vol. 19, pages 125-134 (1994); Matusno et al., Circ. 90, pages 2203-2206 (1994), in in vitro and in vivo models of smooth muscle cell migration and restenosis. The specific $\alpha_v\beta_3$ inhibitors reduced neointima lesion formation, and the peptides which recognize $\alpha_v\beta_3$ and $\alpha_{IIb}\beta_3$ also inhibited neointima formation in these models. Both groups concluded that the $\alpha_v\beta_3$ receptor plays an important role in smooth muscle cell migration.

The involvement of the $\alpha_v\beta_3$ receptor smooth muscle cell migration in bone resorption has been demonstrated using antibody and peptide inhibitors of this integrin receptor. The $\alpha_v\beta_3$ receptor is expressed on osteoclasts, cells which mediate bone resorption through the matrix proteins osteopontin and bone sialoprotein (Miyauchi et al., J. Biol. Chem., Vol. 266, pages 20369-20374; Sato et al., J. Cell. Biol., Vol. 111, pages 1713-1723 (1990); Ross et al., J. Biol. Chem., Vol. 268, pages 9901-9907 (1993). In these publications, the $\alpha_v\beta_3$ specific LM609 antibody and Arg-Gly-Asp containing peptides blocked osteoclast attachment to and resorption on bone particles. These results supported early data by Horton et al. (Exp. Cell Res., Vol. 195, pages 368-375 (1991)) showing disruption of osteoclast function by the 23C6 $\alpha_v$ antibody and Arg-Gly-Asp containing peptide (SEQ ID:16) (GRGDSP). Similarly Law et al., in J. Clin. Invest., Vol. 95, pages 713-724 (1995) confirmed the role of $\alpha_v\beta_3$ in the adherence and migration of cells due to the presence of osteopontin in an RGD-dependent manner.

As described above, peptides that bind to the $\alpha_v\beta_3$ receptor have been demonstrated to inhibit the processes of angiogenesis, smooth muscle cell migration and osteoclast activity. In addition to their binding to the $\alpha_v\beta_3$ receptor, these peptides have one other common determinant: they contain an RGD sequence.

The RGD sequence has been shown to be essential for binding to the $\alpha_v\beta_3$ and other integrin molecules. In 1984, Pierschbacher and Ruoslahti (Proc. Natl. Acad. Sci., Vol. 81, pages 5985-5988) showed that the amino acid sequence arginine, glycine, and aspartic acid or RGD is critical for the role of cell attachment activity essential for the mechanism of many integrins. The binding of $\alpha_v\beta_3$ and other integrins to RGD sequences is reviewed in Ruoslahti and Pierschbacher, Cell, Vol. 44, pages 517-518 (1986) and discussed in Smith et al., J. Biol. Chem., Vol. 265, pages 12267-12271 (1990); Ruoslahti and Pierschbacher, Science, Vol. 238, pages 491-497 (1987); Humphries, J. Cell Sci., Vol. 97, pages 585-92 (1990); Ruoslahti, J. Clin. Invest., Vol. 87, pages 1-5 (1991). Residues adjacent to the RGD can also play a role in binding as shown by Pierschbacher and Ruoslahti, 1987 (J. Bio. Chem., Vol. 262, pages 17924-17928), and the process of cyclizing the RGD peptides can help to improve biological activity. Pierschbacher and Ruoslahti 1987 ibid; Aumailley et al., FEBS, Vol. 291, pages 50-54 (1991); and Koivunen et al., Biotech., Vol. 13, pages 265-270 (1995). Thus, a relationship between activity and conformation has been demonstrated for RGD peptides.

The necessary contribution of the RGD sequence to the inhibitory activity of these peptides for integrins has been demonstrated. Deletion or mutations of the RGD has been shown to abolish activity in Obara et al., Cell, 53, pages 649-657 (1988); Beacham et al., J. Biol. Chem., Vol. 267, pages 3409-3415 (1992); and Cherny et al., J. Biol Chem., Vol. 268, pages 9725-9729 (1993). In fact, variations of RGD peptides such as cyclo RAD and RGE peptides have been traditionally used as negative controls for RGD activity (e.g., Brooks, et al., 1994, ibid. and Nicosia and Bonanno, 1991 ibid.). Additionally, when random cyclic libraries of peptides are screened with various integrins, including $\alpha_5\beta_1$, $\alpha_v\beta_3$, and $\alpha_{IIb}\beta_3$, RGD specific peptides with a variety of ring sizes are identified (Koivunen et al., Biotechnology, Vol.

13, pages 265–270 (1995). Interestingly, when these authors examined the sequences of specific $\alpha_v\beta_3$-binding peptides isolated from their library, four clones which displayed apparent RGD homologs were isolated. In three clones, the glycine residue was substituted by leucine and in 1 clone, serine was substituted for glycine. One of the RLD peptides was synthesized and measured in binding and cell adhesion assays. The peptide (SEQ ID:17) (ACPSRLDSPCG) was only partially selective for the integrin $\alpha_v\beta_3$ and had an activity 100–1000 fold lower than an RGD peptide. Thus the activity of specific antagonists to inhibit the $\alpha_v\beta_3$ receptor in angiogenesis, smooth muscle cell migration and osteoporosis has been demonstrated. Since RGD peptide antagonists can bind and inhibit the activity of a variety of integrin molecules, they may not represent the best diagnostic or therapeutic agents for diseases involving only the $\alpha_v\beta_3$ receptor.

Some RGD sequences within a particular ligand, vitronectin for example, appear to bind to several different integrins such as $\alpha_v\beta_3$, $\alpha_v\beta_5$, $\alpha_v\beta_1$, and $\alpha_{IIb}\beta_3$. We have found certain non-RGD containing peptides show specific binding to $\alpha_v\beta_3$ over other integrins such as $\alpha_v\beta_5$ and $\alpha_{IIb}\beta_3$.

It has now been discovered that certain small peptides of this invention bind to the $\alpha_v\beta_3$ integrin receptor and are useful in inhibiting angiogenesis, treating angiogenic-based diseases, osteoporosis and restenosis. This is particularly surprising in view of the fact that the peptides do not contain an RGD sequence.

OBJECTS OF THE INVENTION

An object of this invention is to provide a peptide that exhibits a high binding affinity for the $\alpha_v\beta_3$ receptor.

Another object of this invention is to provide a peptide that exhibits a high binding affinity for the $\alpha_v\beta_3$ receptor but contains no Arginine-Glycine-Aspartic acid (R-G-D or Arg-Gly-Asp) sequences.

Another object of this invention is to provide a therapeutically useful peptide that exhibits high specificity for binding to the $\alpha_v\beta_3$ receptor as compared to other integrins such as $\alpha_v\beta_3$ and $\alpha_{IIb}\beta_3$.

Another object of this invention is to provide a peptide that is therapeutically useful for treating or preventing disease states that are mediated by the $\alpha_v\beta_3$ receptor as part of the disease process.

Another object of this invention is to provide a method for treating or preventing disease states such as osteoporosis, restenosis, and angiogenic-based diseases.

A more specific object of this invention to provide a method and compositions for treating or preventing disease states such as cancer, inflammatory disorders, rheumatoid arthritis, and other disorders associated with inappropriate or inopportune invasion of blood vessels.

Another object of this invention is to provide a therapeutically useful peptide that can be manufactured using straightforward peptide chemical processes.

Other objects may be apparent to one of ordinary skill in the art upon reading the description of the various aspects of the invention in the following specification.

SUMMARY OF THE INVENTION

One aspect of this invention is a non-RGD nine amino acid cyclic peptide that binds to the $\alpha_v\beta_3$ integrin receptor.

Another aspect of the invention is a non-RGD nine amino acid cyclic peptide that binds to the $\alpha_v\beta_3$ integrin receptor, wherein the cyclic portion contains 5 or 7 amino acid moieties.

Another aspect of the invention is a non-RGD nine amino acid cyclic peptide wherein the cyclic portion includes the sequence, $X_i$-Gly-Ala wherein $X_i$ is Gly, Ala, or Ser.

Another aspect of the invention is a pharmaceutical composition comprising a pharmaceutically acceptable excipient and a peptide of the invention.

Another aspect of the invention is a method of treating a disease that involves the $\alpha_v\beta_3$ integrin receptor, which method comprises administering a therapeutically effective amount of a peptide of the invention sufficient to bind to an $\alpha_v\beta_3$ receptor to treat or prevent such disease.

DESCRIPTION OF SPECIFIC EMBODIMENTS

Definitions

Unless defined otherwise, all technical and scientific terms used herein have the same meaning as commonly understood by one of ordinary skill in the art to which this invention belongs. Generally, the nomenclature used herein and the laboratory procedures described below are those well known and commonly employed in the art. Standard techniques are used for peptide synthesis recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art. The nomenclature used herein and the laboratory procedures in analytical chemistry, organic synthetic chemistry, and pharmaceutical formulation described below are those well known and are used as commonly employed in the art, unless indicated otherwise. Standard techniques are used for chemical syntheses, chemical analyses, pharmaceutical formulation and delivery, and treatment of patients, unless otherwise indicated.

The term "peptide" as used herein means two or more amino acids that are linked together via a peptide bond.

In the formulas representing selected specific peptide embodiments of the present invention, the amino- and carboxy-terminal groups, although often not specifically shown, will be understood to be in the form they would assume at physiological pH values, unless otherwise specified. Thus, the N-terminal $H_2^+$ and C-terminal-$O^-$ at physiological pH are understood to be present though not necessarily specified and shown, either in specific examples or in generic formulas. In the peptide notation used herein, the lefthand end of the molecule is the amino terminal end and the righthand end is the carboxy-terminal end, in accordance with standard usage and convention. Of course, the basic and acid addition salts including those which are formed at nonphysiological pH values are also included in the compounds of the invention.

The term "amino acid" as used herein includes the standard twenty genetically-encoded amino acids and their corresponding stereoisomers in the "D" form (as compared to the natural "L" form), omega-amino acids other naturally-occurring amino acids, unconventional amino acids (e.g. $\alpha,\alpha$- disubstituted amino acids, N-alkyl amino acids, etc.) and chemically derivatized amino acids. When an amino acid is being specifically enumerated, such as "alanine" or "Ala" or "A" the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a three letter designation, corresponding to the trivial name of the conventional amino acid.

In keeping with standard peptide nomenclature (described in *J. Biol. Chem.*, 243: 3552–59 (1969) and adopted at 37 CFR §1.822(b)(2) and (p)(2)). Abbreviations for the 20 genetically-encoded, naturally-occurring amino acid residues are shown in the following Table I:

TABLE I

| AMINO ACID | SYMBOL | |
| --- | --- | --- |
| | 3-Letter | 1-Letter |
| alanine | Ala | A |
| arginine | Arg | R |
| asparagine | Asn | N |
| aspartic acid | Asp | D |
| cysteine | Cys | C |
| glutamic acid | Glu | E |
| glutamine | Gln | Q |
| glycine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |
| tryptophan | Trp | W |
| tyrosine | Tyr | Y |
| valine | Val | V |

Abbreviations for Certain modified and unusual amino acids as shown in Table II and are also included within the definition of "amino acid."

TABLE II

| Abbreviation | Modified and unusual amino acid |
| --- | --- |
| Aad | 2-Aminoadipic acid. |
| bAad | 3-Aminoadipic acid. |
| bAla | beta-Alanine,beta-Aminopropionic acid. |
| Abu | 2-Aminobutyric acid. |
| 4Abu | 4-Aminobutyric acid, piperidinic acid. |
| Acp | 6-Aminocaproic acid. |
| Ahe | 2-Aminoheptanoic acid. |
| Aib | 2-Aminoisobutyric acid. |
| bAib | 3-Aminoisobutyric acid. |
| Apm | 2-Aminopimelic acid. |
| Dbu | 2,4-Diaminobutyric acid. |
| Des | Desmosine. |
| Dpm | 2,2'-Diaminopimelic acid. |
| Dpr | 2,3-Diaminopropionic acid. |
| EtGly | N-Ethylgilycine. |
| EtAsn | N-Ethylasparagine. |
| Hyl | Hydroxylysine. |
| AHyl | allo-Hydroxylysine. |
| 3Hyp | 3-Hydroxyproline. |
| 4Hyp | 4-Hydroxyproline. |
| Ide | Isodesmosine. |
| AIle | allo-Isoleucine. |
| MeGly | N-Methylglycine, sarcosine. |
| MeIle | N-Methylisoleucine. |
| MeLys | N-Methylavaline. |
| Nva | Norvaline. |
| Nle | Norleucine. |
| Orn | Ornithine. |

Certain commonly encountered amino acids, which are not encoded by the genetic code and not shown in Tables I or II, include, for example, other omega-amino acids, such as 3-amino propionic acid, sarcosine (Sar), citrulline (Cit), homoarginine (Har), t-butylalanine (t-BuA), t-butylglycine (t-BuG), phenylglycine (Phg), cyclohexylalanine (Cha), cysteic acid (Cya); pipecolic acid (Pip), thiazolidine (Thz), 2-naphthyl alanine (2-Nal) and methionine sulfoxide (MSO). Examples of unconventional amino acids include: γ-carboxyglutamate, ε-N,N,N-trimethyllysine, ε-N-acetyllysine, O-phosphoserine, N-acetylserine, N-formylmethionine, 3-methylhistidine, 5-hydroxylysine (Hyl), ω-N-methylarginine, and other similar amino acids and imino acids.

It is to be understood that in each of the formulae representing peptides of this invention shown herein, the peptides are cyclical, e.g. having Cys-Cys disulfide bonds forming the cyclic portion. This is true even through the formula may not show a connecting line between the Cys moieties. Thus, the formula

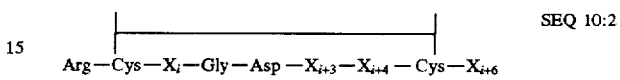

SEQ 10:2 is the same as the formula

SEQ ID:2 Arg-Cys-$X_i$-Gly-Asp-$X_{i+3}$-$X_{i+4}$-Cys-$X_{i+6}$

Non-interfering substituents can be added to free functional groups, including those at the carboxy- or amino-terminus, by amidation, acylation or other substitution reactions. Such substitutions can, for example, change the solubility of the compounds without affecting their activity.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential stearic hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference).

Detailed Description and Preferred Embodiments

A broad aspect of this invention is a nine amino acid peptide that preferably includes a cyclic portion having the sequence $X_i$-Gly-Asp-(SEQ ID:1), wherein $X_i$ is Gly, Ala, or Ser. The peptides of this invention inhibit the function of the $\alpha_v\beta_3$ integrin receptor in various disease states. Thus, the peptides may be combined with a pharmaceutically acceptable excipient to form a pharmaceutical composition useful for treating disease states or conditions that involves the $\alpha_v\beta_3$ receptor.

Compounds of the Invention

As stated above, an aspect of this invention is a nine amino acid peptide that includes a cyclic portion having the sequence $X_i$-Gly-Asp-, wherein $X_i$ is Gly, Ala, or Ser. Aside from the sequence $X_i$-Gly-Asp in the 9 amino acid peptide wherein $X_i$ is Gly, Ala, or Ser, the other positions may be occupied by any amino acid.

In general, however, it is preferred that the amino acids used in the cyclic peptide of this invention are chosen from the twenty, naturally-occurring, genetically-encoded amino acids. Preferred compounds of the invention are presented by the formula SEQ ID:2 Arg-Cys-$X_i$-Gly-Asp-$X_{i+3}$-$X_{i+4}$-Cys-$X_{i+6}$.

Alternatively the formula can be rewritten to emphasize the cyclicity as

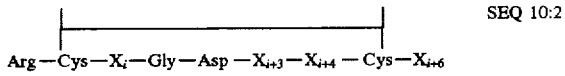

SEQ ID:2 wherein $X_i$ is Gly, Ala, or Ser and $X_{i+3}$, $X_{i+4}$, $X_{i+6}$ are any amino acid.

Preferred peptides also include:

| | |
|---|---|
| SEQ ID:3 | Arg-Cys-Gly-Gly-Asp-Ser-$X_{i+4}$-Cys-$X_{i+6}$ |
| SEQ ID:4 | Arg-Cys-Ala-Gly-Asp-Ser-$X_{i+4}$-Cys-$X_{i+6}$ |
| SEQ ID:5 | Arg-Cys-Gly-Gly-Asp-Asn-$X_{i+4}$-Cys-$X_{i+6}$ |
| SEQ ID:6 | Arg-Cys-Ala-Gly-Asp-Asn-$X_{i+4}$-Cys-$X_{i+6}$ |
| SEQ ID:7 | Arg-Cys-Gly-Gly-Asp-Tyr-$X_{i+4}$-Cys-$X_{i+6}$ |
| SEQ ID:8 | Arg-Cys-Ala-Gly-Asp-Tyr-$X_{i+4}$-Cys-$X_{i+6}$ |
| SEQ ID:9 | Arg-Cys-Gly-Gly-Asp-Thr-$X_{i+4}$-Cys-$X_{i+6}$ |
| SEQ ID:10 | Arg-Cys-Ala-Gly-Asp-Thr-$X_{i+4}$-Cys-$X_{i+6}$ |
| SEQ ID:11 | Arg-Cys-Gly-Gly-Asp-Asp-$X_{i+4}$-Cys-$X_{i+6}$ |
| SEQ ID:12 | Arg-Cys-Ala-Gly-Asp-Asp-$X_{i+4}$-Cys-$X_{i+6}$ | wherein $X_{i+4}$ and $X_{i+6}$ are any amino acid. Especially preferred are sequences wherein $X_{i+4}$ is any genetically encoded amino acid except Gly or Ile, and $X_{i+6}$ is any genetically encoded amino acid except Cys. Most preferred include the sequence (SEQ ID:13) Arg-Cys-Gly-Gly-Asp-Ser-Met-Cys-Tyr.

Chemical derivatives of one or more AA members may be achieved by reaction with a functional side group. Such derivatized molecules include for example those molecules in which free amino groups have been derivatized to form amine hydrochlorides, p-toluene sulfonyl groups, carboxybenzoxy groups t-butyloxycarbonyl groups, chloroacetyl groups or formyl groups. Free carboxyl groups may be derivatized to form salts, methyl and ethyl esters or other types of esters and hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amino terminal acylation (e.g., acetylation or thioglycolic acid amidation), terminal carboxylamidation (e.g., with ammonia or methylamine), and the like terminal modifications.

Terminal modifications are useful, as is well known, to reduce susceptibility by proteinase digestion and therefore to prolong the half-life of the peptides in solutions, particularly in biological fluids where proteases may be present.

Polypeptide cyclization is also a useful modification and is preferred also because of the stable structures formed by cyclization and in view of the biological activities observed for cyclic peptides.

Identification and Chemical Synthesis of the Invention Peptides

With the teachings of this specification in hand, one skilled in the art can understand how the peptide antagonists of $\alpha_v\beta_3$ via are identified by panning phage-display peptide libraries with the receptor attached to a solid support, for example small diameter (1 μm) polystyrene latex beads. Phage selected by this method can then be tested for specific binding to $\alpha_v\beta_3$ via ELISA or other immunologically-based assays. Individual peptide sequences are then determined via sequencing of phage DNA. Further analysis of the minimal peptide sequence required for binding can be assessed via deletion and site-directed mutagenesis, followed by testing of the phage for binding to $\alpha_v\beta_3$ via ELISA. Since the identified peptide candidates are fused to the major phage coat protein, soluble peptides are then chemically synthesized and the activity of these free peptides tested in various in vitro an in vivo assays for the ability to act as antagonists of the $\alpha_v\beta_3$ receptor. A general discussion of epitope, or peptide, libraries by Jamie K. Scott is found at TIB517, July 1992, p 241–245. A specific process for synthesizing the oligonucleotides is set forth in U.S. Pat. No. 5,264,563 issue Nov. 23, 1993 to Huse. A related process is presented in an article by Koivunen, et. al., *J. Cell Bio*, 124: 373–380 (1994). These are each incorporated herein by reference.

The general foregoing description may be modified to emphasize a preferred aspect of the invention, i.e. the presence of Cys groups to form Cys-Cys double bonds. Cysteine-doped phage-display peptide libraries are constructed using codon-based mutagenesis as per the Huse patent. These libraries consist of a mixture of approximately $10^9$ random peptides which are 20 amino acids in length and which have a greater than 1 in 20 chance of containing a cysteine residue at most positions. This provides for peptides which are biased toward being conformationally constrained by disulfide bonds and thus are more likely to bind with higher affinity to $\alpha_v\beta_3$ compared with linear peptides. Also, by using the codon-based mutagenesis technology, phage-display peptide libraries can be constructed which are biased toward peptides that lack the known tripeptide sequence RGD. This type of library increased the frequency of identifying non-RGD containing peptides. This is of some importance, since part of this invention is the discovery that non-RDG containing peptides afford greater selectivity in binding to $\alpha_v\beta_3$ over other integrin molecules which are known to interact well with proteins or peptides which contain an RGD tripeptide.

A peptide of this invention can be synthesized by several methods, including chemical synthesis and recombinant DNA techniques. Synthetic chemistry techniques, such as solid phase Merrifield synthesis are preferred for reasons of purity, freedom from undesired side products, ease of production, etc. A summary of the techniques available are found in several articles, including Steward et. al., *Solid Phase Peptide Synthesis*, W. H. Freeman, Co., San Francisco (1969); Bodanszky, et. al., *Peptide Synthesis*, John Wiley and Sons, Second Edition (1976); J. Meienhofer, *Hormonal Proteins and Peptides*, 2: 46, Academic Press (1983); Merrifield, *Adv. Enzymol.* 32: 221–96 (1969); Fields, et. al., *Int 1. Peptide Protein Res.*, 35: 161–214 (1990) and U.S. Pat. No. 4,244,946 for solid phase peptide synthesis and Schroder et al., *The Peptides*, Vol. 1, Academic Press (NY) (1965), for classical solution synthesis. Protecting groups usable in synthesis are described as well in *Protective Groups in Organic Chemistry*, Plenum Press, New York (1973). Solid phase synthesis methods consist of the sequential addition of one or more amino acid residues or suitably protected amino acid residues to a growing peptide chain. Either the amino or carboxyl group of the first amino acid residue is protected by a suitable selectively removable protecting group. A different, selectively removable protecting group is utilized for amino acids containing a reactive side group such as lysine.

Using a solid phase synthesis method, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is mixed with the solid support and reacted to form an amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently to yield the final desired peptide.

The resultant linear peptides may then be reacted to form their corresponding cyclic peptides. A method for cyclizing peptides is described in Zimmer, et.al., *Peptides*, 393–394 (1992), ESCOM Science Publishers, B.V., 1993. Typically, tertbutoxycarbonyl protected peptide methyl ester is dissolved in methanol and sodium hydroxide solution are added and the mixture treated at 20° C. to hydrolytically remove the methyl ester protecting groups. After evaporating the solvent, the tertbutoxycarbonyl protecting groups are then removed under mildly acidic conditions in dioxane cosolvent. The deprotected linear peptide with free amino and carboxy termini is then converted to its corresponding cyclic peptide by reacting a dilute solution of the linear peptide in a mixture of dichloromethane and dimethylformamide, with dicyclohexylcarbodiimide in the presence of 1-hydroxybenzotriazole and N-methylmorpholine. The resultant cyclic peptide is then purified by chromatography. Another method to cyclize peptides is described by Gurrath et al, *Eur. J. Biochem* 210: 911–921 (1992).

To cyclize peptides containing two or more cysteines through the formation of disulfide bonds, the methods described by Tam, et al, *J. Am. Chem. Soc.*, 113: 6657–6662 (1991); Plaue, *Int. J. Peptide Protein Res.*, 35: 510–517 (1990); Atherton, *J. Chem. Soc. Trans.* 1: 2065 (1985); B. Kamber, et. al. *Helv. Chim. Acta* 63: 899 (1980) are appropriate. Typically, peptides are cyclized in an aqueous, buffered environment having a pH appropriate for cyclization (8–9) at low concentration (0.01–10.0 µM). For example, cyclization occurs in 50 mM Tris, pH 8.5 at a concentration of 0.1–1 µM peptide by bubbling $CO_2$ depleted air through a solution of peptide for 48 hours prior to drying and purification by reverse phase HPLC. This cyclization procedure can be performed before or after cleavage from the solid support. Selective cyclization of cysteine pairs in peptides containing more than two cysteines can be performed using specific protecting groups for desired pairs of cysteines. For example, a combination of two cysteine residues protected with a trityl group (trt) and two cysteine residues protected with an acetamidomethyl group (Acm) in a peptide allows the formation of Cys (trt) disulfide bonds after the initial deprotection of the peptide with trifluoroacetic acid treatment. Subsequently, the Cys (Acm) groups can be deprotected and oxidized at a later stage by a different deprotection and cyclization scheme suitable for the Acm group, such as iodine treatment. Purification of selectively cyclized peptides is then accomplished by reverse phase HPLC as for other peptides.

Peptides may be in the form of any pharmaceutically acceptable salt. Acids capable of forming salts with peptides include inorganic acids such as trifluoroacetic acid (TFA), hydrochloric acid, perchloric acid, nitric acid, thiocyanic acid, sulfuric acid, phosphoric acid, acetic acid, propionic acid, oxalic acid, glycolic acid, lactic acid, pyruvic acid, malonic acid, succinic acid, maleic acid, fumaric acid, anthranilic acid, cinnamic acid, naphthalene sulfonic acid, sulfanilic acid or the like. Hydrochloric acid and trifluoroacetic acid salts are preferred. Suitable bases capable of forming salts with the peptides of the present invention include inorganic bases such as sodium hydroxide and the like as well as organic bases such as mono-, di- and tri-alkyl and aryl amines (e.g., triethylamine, diisopropyl amine, methyl amine, dimethyl amine and the like) and optionally substituted ethanolamines (e.g. ethanolamine, diethanolamine, and the like).

Recombinant Production

Alternatively, selected compounds of the present invention are produced by expression of recombinant DNA constructs prepared in accordance with well-known methods once the peptides are known. Such production can be desirable to provide large quantities or alternative embodiments of such compounds. Since the peptide sequences are relatively short, recombinant production is facilitated; however, production by recombinant means is preferred over standard solid phase peptide synthesis for peptides of at least 8 amino acid residues.

The DNA encoding the sequenced compounds of the present invention is preferably prepared using commercially available nucleic acid synthesis methods. Following these nucleic acid synthesis methods, DNA is isolated in a purified form which encodes the peptides of the invention. Methods to construct expression systems for production of peptides of the invention in recombinant hosts are also generally known in the art. Preferred recombinant expression systems, when transformed into compatible hosts, are capable of expressing the DNA encoding the peptides of the invention. Other preferred methods used to produce peptides of the invention comprise culturing the recombinant host under conditions that are effective to bring about expression of the peptides encoding DNA to produce the peptide of the invention and ultimately recovering the peptides from the culture.

DNA encoding a peptide of this invention, is readily isolated and sequenced using conventional procedures. The recombinant hosts described herein serve as a preferred source of such DNA. Once isolated, the DNA may be placed into expression vectors, which are then transferred into host cells.

Expression can be effected in either procaryotic or eucaryotic hosts. Procaryotes most frequently are represented by various strains of E. coli. However, other microbial strains may also be used, such as bacilli, for example Bacillus subtilis, various species of Pseudomonas, or other bacterial strains. In such procaryotic systems, plasmid vectors which contain replication sites and control sequences derived from a species compatible with the host are used. For example, a workhorse vector for E. coli is pBR322 and its derivatives. Commonly used procaryotic control sequences, which contain promoters for transcription initiation, optionally with an operator, along with ribosome binding-site sequences, include such commonly used promoters as the beta-lactamase (penicillinase) and lactose (lac) promoter systems, the tryptophan (trp) promoter system, and the lambda-derived $P_L$ promoter and N-gene ribosome binding site. However, any available promoter system compatible with procaryotes can be used.

Expression systems useful in eucaryotic hosts comprise promoters derived from appropriate eucaryotic genes. A class of promoters useful in yeast, for example, includes promoters for synthesis of glycolytic enzymes, e.g., those for 3-phosphoglycerate kinase. Other yeast promoters include those from the enolase gene or the Leu2 gene obtained from YEp13.

Suitable mammalian promoters include the early and late promoters from SV40 or other viral promoters such as those derived from polyoma, adenovirus II, bovine papilloma virus or avian sarcoma viruses. Suitable viral and mammalian enhancers are cited above. In the event plant cells are used as an expression system, the nopaline synthesis promoter, for example, is appropriate.

The expression systems are constructed using well-known restriction and ligation techniques and transformed into appropriate hosts. A preferred expression system would be, when transformed into a compatible host, capable of expressing a DNA encoding a peptide of the invention and inhibiting the binding of the $\alpha_v\beta_3$ integrin receptor with substantially more potency than the natural ligand to the $\alpha_v\beta_3$ integrin receptor. This expression system would comprise peptides of the invention containing the amino acid sequence of formula (I).

Transformation is done using standard techniques appropriate to such cells. The cells containing the expression systems are cultured under conditions appropriate for production of the peptides, and the peptides are then recovered and purified.

Antibodies

The availability of the purified peptide of the invention also permits the production of antibodies specifically immunoreactive with these forms of the active peptide.

The compositions containing purified peptide can be used to stimulate the production of antibodies which immunoreact with the peptides. Standard immunization protocols involving administering peptide to various vertebrates, such as rabbits, rats, mice, sheep, and chickens result in antisera which are immunoreactive with the purified peptide. A peptide may be advantageously conjugated to a suitable antigenically neutral carrier, such as an appropriate serum albumin or keyhole limpet hemocyanin, in order to enhance immunogenicity. In addition, the free peptide can be injected with methylated BSA as an alternative to conjugation. Furthermore, the antibody-secreting cells of the immunized mammal can be immortalized to generate monoclonal antibody panels which can then be screened for reactivity with peptide.

The resulting polyclonal or monoclonal antibody preparations are useful in assays for levels of the corresponding peptide in biological samples using standard immunoassay procedures.

Administration and Utility

Another aspect of this invention is a method for treating a disease that involves the $\alpha_v\beta_3$ integrin receptor by administering a therapeutically effective amount of a peptide of this invention to a patient in need thereof. Generally that amount is sufficient to bind to the $\alpha_v\beta_3$ receptor in a manner that effectively treats and/or prevents the disease. Diseases involving the $\alpha_v\beta_3$ integrin receptor include angiogenic-based diseases (e.g., cancer, anti-inflammatory diseases, retinal neuvascular disease, and macular degeneration diseases), diseases related to smooth muscle cell migration (e.g. restenosis) and diseases related to osteoclast-mediated bone resorption (e.g. osteoporosis).

As pointed out, the peptides of the invention are useful therapeutically, to inhibit angiogenesis, i.e. the formation of new blood vessels. Another term for such angiogenesis is neovascularization. Angiogenesis, or neovasculization, includes a variety of processes including "sprouting", vasculogenesis, or vessel enlargement, all of which are mediated by and dependent upon $\alpha_v\beta_3$ interaction. With the exception of traumatic wound healing, corpus leuteum formation and embryogenesis, it is believed that the majority of angiogenic processes are associated with and/or facilitate a variety of disease processes and states. By inhibiting angiogenesis, therefore, one can intervene in the disease process or state, prevent the disease, ameliorate the signs and symptoms, and in some cases, cure the disease. Compounds of this invention can be referred to as "antineovascularization agents" or "antiangiogenic agents."

The diseases in which angiogenesis is believed to be important, referred to as angiogenic diseases, include, but are not limited to, inflammatory disorders such as immune and non-immune inflammation, chronic articular rheumatism and psoriasis, rheumatoid arthritis, disorders associated with inappropriate or inopportune invasion of vessels such as diabetic retinopathy, neovascular glaucoma, macular degeneration, capillary proliferation in atherosclerotic plaques and osteoporosis, and cancer associated disorders, such as solid tumors, solid tumor metastases, angiofibromas, skin cancer, retrolental fibroplasia, hemangiomas, Kaposi's sarcoma and like cancers that require neovascularization to support tumor growth. To the extent that the compounds of this invention are useful for treating, inhibiting or preventing cancerous tumor growth, they may be referred to as antineoplastic drugs.

The peptides of this invention are also useful therapeutically to treat and/or prevent undesirable smooth muscle cell migration/proliferation. Specific $\alpha_v\beta_3$ inhibitors reduce neointima lesion formation. The results of such smooth muscle cell migration are often seen in the occlusion of blood vessels after angioplasty. This process of occlusion of the vessels is referred to as restenosis and is a major problem in patients who have angioplasty performed.

The peptides of this invention are also useful therapeutically to treat and/or prevent diseases related to osteoclast-mediated bone resorption. Bone resorption requires the tight attachment of osteoclasts (bone-resorbing cells) to the bone mineralized matrix. Osteoclasts are thought to express, i.a., $\alpha_v\beta_3$ on their surfaces that interacts with a ligand to provide a signal for the process to go forward. While not wanting to be bound by any theory, the peptides of this invention are thought to bond to $\alpha_v\beta_3$ and effectively block the bone resorption process. Thus, the peptides of this invention are useful for treating and/or preventing osteoporosis, a disease of particular importance in an aging population. The use of the compounds of this invention can be used alone or in combination with other therapies that focus on restoring the balance between bone resorption and bone formation (e.g., the use of estrogens, calcitonin, calcium supplements, vitamin D, bisphosphonates, synthetic PTH analogs, etc.)

The peptides of this invention may be therapeutically useful in other disease states that involve $\alpha_v\beta_3$ but that are not specifically disclosed herein but which are apparent to one of ordinary skill upon reading this application in light of other knowledge available in the art. Insofar as that is the case, the treatment of such disease state is meant to be encompassed herein.

In determining whether a peptide of this invention may be useful in the method of this invention one may use any of the available in vitro or in vivo assays available to those skilled in the art. In vitro assays to evaluate the activities of peptide antagonists of the $\alpha_v\beta_3$ integrin receptor include a ligand binding assay using a solid phase ELISA, which is described in the Examples and referenced in Felding-Haberman et al., *J. Biol. Chem.*, Vol. 267, pages 5070–5077 (1992) and Orlando, R. A. and Cheresh, D. A. *J. Biol. Chem.* Vol. 266, pages 19543–19550 (1991). Another in vitro assay includes a cell adhesion assay that shows whether a compound inhibits the ability of $\alpha_v\beta_3$-expressing tumor cells (e.g. M21 melanoma cells) to adhere to vitronectin or fibrinogen. If a compound prevents a cell from adhering, it has the potential to inhibit angiogenesis or metastasis. This is further described in detail in the Examples. See also D. A. Cheresh et al., *Cell*, 57: 59–69 (1989); N. Kieffer et al., *J. Cell Biol.*, 113, Number 2: 451–461 (1991); and B. Felding-Haberman et al., *J. Clin. Invest.*, 89: 2018–2022 (1992). Another in vitro assay contemplated includes the tubular cord formation assay. This in vitro assay shows growth of new blood vessels at the cellular level. See D. S. Grant et al., *Cell*, 58: 933–943 (1989) and C. M. Davis et al., *J. Cell. Bioc.*, 51: 206–218.

The peptides of the invention may be tested in certain well-accepted in vivo assays in various test animals such as chickens, rats, mice, rabbits and the like. These in vivo assays include the chicken chorioallantoic membrane (CAM) assay. This assay has been used to show antiangiogenic activity of both normal and neoplastic tissues. See, D. H. Ausprunk, *Amer. J. Path.*, 79, No. 3: 597–610 (1975) and L. Ossonowski and E. Reich, *Cancer Res.*, 30: 2300–2309 (1980). Other in vivo assays include the mouse metastasis assay, which shows the ability of a compound reduce the rate of growth of transplanted tumors in certain mice or to inhibit the formation of tumors or preneoplastic cells in mice predisposes to cancer or chemically-induced cancer. See M. J. Humphries et al., *Science*, 233: 467–470 (1986) and M. J. Humphries et al., *J. Clin. Invest.*, 81: 782–790 (1988).

While the primary "patient" to whom a compound of this invention is administered will be a human, both male and female, it is to be understood that the compounds of this invention may also be administered to other mammals. These include domestic animals such as dogs, cats and horses as well as livestock such as cows, pigs, goats and the like. Thus the compounds of the invention may be administered by human health professionals as well as veterinarians. In such patients, whether human or otherwise, any variety of tissues or organs can support the disease conditions the peptides of this invention are designed to treat. These tissues and organs include skin, muscle, gut, connective tissue, joints, bones, blood vessels, etc.

Another related aspect of the invention is a method for administering a compound of this invention, in conjunction with other therapies such as conventional drug therapy chemotherapy directed against solid tumors and for control of establishment of metastases. The administration of a peptide of this invention is typically conducted during or after chemotherapy, although it is preferable to inhibit angiogenesis after a regimen of chemotherapy at times where the tumor tissue will be responding to the toxic assault. The tumor will attempt to induce angiogenesis to recover by the provision of a blood supply and nutrients to the tumor tissue. Such recovery will be thwarted by the administration of compounds of this invention. In addition, it is preferred to administer a peptide of this invention after surgery where solid tumors have been removed as a prophylaxis against future metastases.

One of ordinary skill will recognize that the potency, and therefore a "therapeutically effective" amount can vary for the compounds of this invention. However, as shown by this specification one skilled in the art can readily assess the potency of a candidate peptide of this invention. Potency can be measured by a variety of means including inhibition of angiogenesis in the CAM assay referred to herein, inhibition of binding of natural ligand to $\alpha_v\beta_3$ as described herein, and the like assays. For example a peptide of this invention has the ability to substantially inhibit binding of a natural ligand such as fibrinogen or vitronectin to $\alpha_v\beta_3$ in solution. "Substantial inhibition" is inhibition at an antagonist concentration of less than 10 micromolar (μM), preferably less than 1.0 μM, more preferably less than 0.1 μM, and most preferably less than 0.05 μM. Inhibition is meant that at least a 50 percent reduction in binding of fibrinogen is observed by inhibition in the presence of the $\alpha_v\beta_3$ antagonist, and at 50% inhibition is referred to herein as an $IC_{50}$ value.

A unique characteristic of the peptides of this invention particularly the preferred peptides, is that they exhibit selectivity for $\alpha_v\beta_3$ over other integrins. Thus, the preferred peptides antagonist substantially inhibit fibrinogen binding to $\alpha_v\beta_3$ but does not substantially inhibit binding of fibrinogen to another integrin, such as $\alpha_v\beta_1$, $\alpha_v\beta_5$ or $\alpha_{IIb}\beta_3$. Particularly preferred is an $\alpha_v\beta_3$ antagonist that exhibits a 10-fold to 100-fold lower $IC_{50}$ activity at inhibiting fibrinogen binding to $\alpha_v\beta_3$ compared to the $IC_{50}$ activity at inhibiting fibrinogen binding to another integrin. An exemplary assay for measuring $IC_{50}$ activity at inhibiting fibrinogen binding to an integrin is described in Example 1.

The peptides of this invention are administered to a patient in need thereof by commonly employed methods for administering peptides in such a way to bring the peptide in contact with the tissue to be treated. Such methods include oral administration, parenteral injection (IP), subcutaneous injection (SC—particularly a controlled release depot), intravenous injection (IV), intramuscularly (IM) and intranasal (IN) or oral inhalation (OI). In general, a therapeutically effective amount is that amount needed to achieve the desired results, i.e. prevent angiogenesis (neovascularization), smooth cell migration (restenosis), or osteoporosis through antagonizing the $\alpha_v\beta_3$ receptor and thus successfully treating of the targeted disease state.

The dosage ranges for the administration of the a peptide of this invention (the $\alpha_v\beta_3$ antagonist) depend upon the form of the antagonist, and its potency, as described further herein, and are amounts large enough to produce the desired effect in which the disease symptoms mediated by angiogenesis are ameliorated, e.g. angiogenesis is measurably prevented, inhibited or decreased. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can also be adjusted by the individual physician in the event of any complication.

A therapeutically effective amount of a peptide of this invention is typically an amount of polypeptide such that when administered in a physiologically tolerable composition is sufficient to achieve a plasma concentration of from about 0.1 nanogram (ng) per milliliter (ml) to about 200 µg/ml, preferably from about 1 ng/ml to about 100 µg/ml. The dosage per body weight can vary from about 0.01 mg/kg to about 3 mg/kg, and preferably from about 0.1 mg/kg to about 1 mg/kg, in one or more dose administrations daily, for one or several days.

The therapeutic compositions containing a peptide of this invention are conventionally administered, whether by IP, IM, IV, INI, SubCu, or OI, as of a unit dose. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

Because of the well-known instability of peptide in the gastrointestinal tract, the compounds of this invention are preferably administered IV, IM, IP, SubCu, IN or OI. Most preferably the compounds are administered IP using a controlled release delivery or are administered by a noninvasive route. Articles by George Hiller, *Advanced Drug-Delivery Reviews*, 10: 163–204 (1993) [Elsevier Science Publishers B.V.] and Lorraine L. Wearley, *Critical Reviews in Therapeutic Drug Carrier Systems*, 8(4): 331–394 (1991) are useful discussions of these types of administrations. These articles are incorporated herein by reference.

Dosage Forms

Another aspect of this invention is a pharmaceutically-acceptable therapeutic composition that comprises a therapeutically effective amount of a peptide of this invention in combination with a pharmaceutically-acceptable excipient. The composition is designed to facilitate the method of administering a peptide of this invention in an effective manner. Generally a composition of this invention will have a peptide dissolved or dispersed in the pharmaceutically-acceptable excipient.

As used herein, the terms "pharmaceutically acceptable", "physiologically tolerable" and grammatical variations thereof, as they refer to compositions, excipients (including carriers, diluents, stabilizers, lubricants, reagents and the like), are used interchangeably and represent that the materials are capable of administration to or upon a mammal without the production of undesirable physiological effects such as nausea, dizziness, gastric upset and the like.

Compounds of this invention may be administered to a mammalian host in a variety of forms depending on the method of administration. The method of administration may be viewed as "invasive" (e.g., IV, IM, IP or SC) or "non-invasive" (e.g., ocular, buccal, oral, transdermal, rectal, NI, OI [pulmonary], and the like). In general, a composition that is delivered by an invasive route is generally administered by a health care professional while a composition delivered by a non-invasive route may be administered by the patient him- or herself.

Compositions that are administered by an invasive route may be designed to be immediate-release or controlled-release over a period of time. Because proteins may be rapidly deactivated by proteolytic enzymes, it is preferable to employ a controlled release dosage form. Nonetheless, immediate release composition may be used. To aid one of skill the art in determining the peptide stability in different biological media and providing guidance as to the type of delivery system to employ, the following articles are useful: Powell, et al, *J. Pharm. Sci.*, 81(8): 731–735 (August, 1992) and Powell, et al., *Pharm Res.*, 10(9): 1268–1273 (1993).

In administering the compounds of the invention by non-invasive method there are various general methods that are used for enhancing the delivery of proteins. The first is to increase the absorption of the protein. This can be done by the use of a prodrug, chemical modification of the primary structure of the compound, incorporation of the compound into liposomes or other encapsulation material, co-administration with penetration enhancers, the use of physical methods such as iontophoresis and phonophoresis and targeting to specific tissues. Another method for enhancing protein delivery is to minimize the metabolism of the protein. This would include chemical modification of the primary structure, covalent attachment to a polymer, incorporation into a liposome or other encapsulation material, co-administration with an enzyme inhibitor and targeting to specific tissues. The third general method of enhancing protein delivery includes prolonging the half-life of the peptide by protecting it with polymers or liposomes, using a bioadhesive material or targeting the composition to a specific tissue.

In general, if it is desired to increase the absorption of the peptide of this invention through ocular, buccal, transdermal, rectal, nasal inhalation or oral inhalation one can employ certain penetration enhancers. These enhancers can include chelators such as EDTA, citric acid, N-acyl derivatives of collagen, enamines (N-Amino N-acyl derivatives of β-diketones). Surfactants can also be used to enhance penetration. These include, sodium lauryl sulfate, polyoxyethylene-9-lauryl ether and polyoxyethelene-20-cetyl ether. Bile salts and derivatives are also known to enhance the penetration of peptides and these include, sodium deoxycholate, sodium glycocholate, sodium taurocholate, sodium taurodihydrofusidate and sodium glycodihyrofusidate. Still another type of penetration enhancer useful in the composition of this invention includes ceratin fatty acids and derivatives such as oliec, caprylic acid, capric acid, acylcarnitines, acylcholine and mono and diglycerides. Nonsurfactants are also useful as penetration enhancers. The penetration enhancers can be used in the solution with the compounds of this invention where the compound and the penetration enhancers are in a pharmaceutically acceptable sterile solution which can be administered, for example by nasal administration. Alternatively the penetration enhancers can be included in a powered formulation that can be administered as a aerosol by suspending the particulate matter in the stream of air and having the patient inhale the suspended particles. Such powered formulations can be administered by a dry-powder inhaler such as those represented by Ventolin Rotohaler (Glaxo, Inc., Research Triangle Park, N.C. U.S.A), and Spinhaler (Fisons Corporation, Bedford, Mass.). Compositions that are in the form of solid micronized particle having a particle size of about 0.5 to 10 microns in median diameter maybe prepared in accordance with the teaching of PCT application international publication numbers WO91/16038 and WO93/00951. Powders may be prepared in accordance with the teaching of Remingtons Pharmaceutical Sciences, 18th Edition, Mack Publishing Co., Chapter 88: 1645–1648. These are in incorporated herein by reference.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. In preparing oral formulations one needs to be aware of the problems of degradation in the mouth and upper GI tract. Thus, it may be preferable to employ an enzyme inhibitor in combination with the peptide, to use a penetration enhancer or to use a protective polymer or microcapsule. The percentage of the compositions and preparations may, of course, be varied and may conveniently contain up to about 20% by weight of the peptide in a dosage unit. The amount of active compound in such therapeutically useful compositions is such that a suitable dosage will be obtained. Preferred compositions or preparations according to the present invention are prepared so that an oral dosage unit form contains between about 0.1 and 50 mg of active compound.

The tablets, troches, pills, capsules and the like may also contain excipients such as the following: a binder such as polyvinylpyrrolidone, gum tragacanth, acacia, sucrose, corn starch, gelatin, calcium phosphate, sodium citrate, and calcium carbonate; a disintegrant such as corn starch, potato starch, tapioca starch, certain complex silicates, alginic acid and the like; a lubricant such as sodium lauryl sulfate, talc and magnesium stearate; a sweetening agent such as sucrose, lactose or saccharin; or a flavoring agent such as peppermint, oil of wintergreen or cherry flavoring. Solid compositions of a similar type are also employed as fillers in soft and hard-filled gelatin capsules; materials in this connection also include lactose or milk sugar as well as high molecular weight polyethylene glycols. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye, flavoring such as cherry or orange flavor, emulsifying agents and/or suspending agents, as well as such diluents as water, ethanol, propylene glycol, glycerin and various like combinations thereof. Of course, any material used in preparing any dosage unit form should be pharmaceutically pure and substantially non-toxic in the amounts employed. In addition, the active compound may be incorporated into sustained-release preparations and formulations. Further components may be apparent to one of ordinary skill in the art.

For purposes of IP administration, solutions in sesame or peanut oil or in aqueous propylene glycol can be employed, as well as sterile aqueous solutions of the corresponding water-soluble, alkali metal or alkaline-earth metal salts. Such aqueous solutions should be suitable buffered and the liquid diluent first rendered isotonic with sufficient saline or glucose. Solutions of the active compound as a free base or a pharmacologically acceptable salt can be prepared in water suitably mixed with e.g. hydroxypropylcellulose. A dispersion can also be prepared in glycerol, liquid polyethylene glycols and mixtures thereof and in oils. Under ordinary conditions of storage and use, these preparations contain a preservative to prevent the growth of microorganisms. These particular aqueous solutions are especially suitable for IV, IM, SC and IP. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from the previously sterile-filtered solution thereof.

For IP formulations that are controlled-release, a peptide of this invention is combined with a polymer that regulates the release of the peptide and protects it from degradation. Generally such polymer may be biodegradable or non-biodegradable and may further by hydrophilic or hydrophobic. Suitable hydrophilic, non-degradable polymers for use in the composition of this invention include hydrogels such as acrylamide or vinyl pyrrolidone crosslinked with N, N'-methylene bisacrylamide. Suitable non-degradable hydrophobic polymers include, ethylene/vinyl acetate copolymers, silicone elastomers, polydimethylsiloxane, and the like. Degradable hydrophilic polymers useful in this invention include N-vinyl pyrrolidone or acrylamide crosslinked with less than 1% N, N'- methylene bisacrylamide, dextran derivatized with glycidyl methacrylate and crosslinked with N, N'- methylene bisacrylamide, water-soluble polyester prepared from fumaric acid and poly (ethylene glycol) and crosslinked with N-vinyl pyrrolidone, water-soluble polyesters, and the like. Suitable degradable hydrophobic polymers useful for the composition of this invention include lactide/glycolide co-polymers, poly (orthoesters) and polyanhydrides. Of these various polymers, the lactide/glycolide co-polymers are preferred. A more detailed description of these polymers for controlled parenteral delivery of peptides may be found in an article by George Heller, *Advanced Drug-Delivery Reviews*, 10: 163–204 (1993) (Elsevier Science Publishers BV). The article is incorporated herein by reference.

For the preferred controlled release composition of this invention the lactide/glycolide co-polymers may have a ratio of DL-a lactic acid to DL-glycolic acid of about 30:70 to about 70:30, preferably about 40:60 to about 60:40. A ratio of about 44:56 is representative. Generally a peptide of this invention is microencapsulated in the copolymer by means known in the art to form the composition, see, for example, U.S. Pat. No. 4,675,189 issued Jun. 23, 1987 to Sanders, Kent, Lewis and Tice. The active peptide is present in an amount from about 0.5% by weight (% w) to about 20.0% w, preferably about 1.0% w to about 10.0% w.

For purposes of topical administration, dilute sterile, aqueous solutions (usually in about 0.1% to 5% concentration), otherwise similar to the above parenteral solutions, are prepared in containers suitable for drop-wise administration to the eye.

The dosage of the present therapeutic agents which will be most suitable for prophylaxis or treatment will vary with the form of administration, the particular compound chosen and the physiological characteristics of the particular patient under treatment. Generally, small dosages will be used initially and, if necessary, will be increased by small increments until the optimum effect under the circumstances is reached. Oral administration requires higher dosages.

Diagnostic Method

Another aspect of this invention is a method for determining the presence of a disease that involves the $\alpha_v\beta_3$ integrin receptor. The method comprises (a) contacting a cell extract from a tissue sample suspected of harboring such disease with measured quantity of a peptide of five to about thirty amino acid moieties, wherein the peptide includes a cyclic portion that contains five to fourteen amino acid moieties; includes no -Arg-Gly-Asp- sequence; includes an amino acid sequence Arg-$X_6$-Asp- where $X_6$ is any naturally occurring amino acid except Gly; and wherein the amino acid moieties external of the cyclic portion do not interfere with binding to the $\alpha_v\beta_3$ integrin receptor;

(b) determining the level of binding of the peptide to the $\alpha_v\beta_3$ integrin receptor; and (c) comparing the level of binding in (b) to a standard level of binding of said peptide to a cell extract from a healthy tissue sample.

A high level of binding of the peptide to the "diseased" tissue sample indicated the likely presence of an angiogenic-based disease state, an osteoclast-mediated disease state such as osteoporosis or a smooth-muscle cell migration disease state such as restenosis. To determine the level of binding, the peptide is labelled with a detectable label such as a fluorescent or radioactive label. It is to be understood that the compounds preferred for the diagnostic method and kit of this invention are those that are preferred in the same manner as disclosed under the section of this specification entitled "Compounds of the Invention." The diagnostic method of this invention may be of a competitive or non-competitive nature, as those terms are understood in the art.

Another aspect of this invention is a diagnostic kit that includes, in an amount sufficient for at least one assay, a peptide of this invention or a polyclonal antibody or monoclonal antibody of the present invention as a separately packaged reagent. Instructions for use of the packaged reagent are also typically included. Instructions for use typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, a diagnostic system for assaying for the specific presence of the $\alpha_v\beta_3$ integrin receptor in a host sample, such as blood, plasma, or tumor cells, comprises a package containing a subject polyclonal antibody that immunoreacts with a polypeptide corresponding to formula (I). In another embodiment, a diagnostic system for assaying for the specific presence of the $\alpha_v\beta_3$ integrin receptor in a host sample comprises a package containing a subject monoclonal antibody that immunoreacts with an epitope formed by the $\alpha_v\beta_3$ integrin receptor-binding region, and preferably also immunoreacts with a polypeptide corresponding to formula (I). A diagnostic system may also include a subject polypeptide where the assay method to be performed by the diagnostic system utilizes a competitive immunoreaction format. Further preferred are kits wherein the antibody molecules of the polyclonal or monoclonal antibody are linked to a label.

Thus, in preferred embodiments, a diagnostic system of the present invention further includes a label or indicating means capable of signaling the formation of a complex containing the antibody molecules of a polyclonal or monoclonal antibody of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. "In Vivo" labels or indicating means are those useful within the body of a human subject and include $^{111}$In, $^{99}$Tc, $^{Ga,186}$Re, and $^{132}$I. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel protein methods and/or systems.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol,* 73: 3–46 (1981). The techniques of protein conjugation or coupling through activated functional groups are particularly applicable. See, for example, Aurameas, et al., *Scand. J. Immunol.,* 8 Suppl. 7: 7–23 (1978); Rodwell et al., *Biotech.,* 3: 889–894 (1984) and U.S. Pat. No. 4,493,795.

The diagnostic systems can also include, preferably as a separate package, a specific binding agent. A "specific binding agent" is a molecular entity capable of selectively binding a reagent species of the present invention but is not itself a protein expression product, polypeptide, or antibody molecule of the present invention. Exemplary specific binding agents are antibody molecules, complement proteins or fragments thereof, protein A and the like. Preferably, the specific binding agent can bind the antibody molecule or polypeptide of this invention when it is present as part of a complex.

In preferred embodiments the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the presence or specific quantity of the $\alpha_v\beta_3$ integrin receptor in a body fluid sample such as serum, plasma or urine. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; U.S. Pat. No. 3,850,752; and U.S. Pat. No. 4,016,043, which are all incorporated herein by reference.

Thus, in preferred embodiments, the expressed peptide, or antibody molecule of the present invention can be affixed to a solid matrix to form a solid support that is separately packaged in the subject diagnostic systems.

The reagent is typically affixed to the solid matrix by adsorption from an aqueous medium although other modes of affixation, well known to those skilled in the art can be used.

Useful solid matrices are well known in the art. Such materials include the cross-linked medium although other modes of affixation, well known to those skilled in the art can be used.

Useful solid matrices are well known in the art. Such materials include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microliter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microliter plate and one or more buffers can also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles, vials, plastic and plastic-foil laminated envelopes and the like.

The invention now being generally described, the same will be better understood by reference to the following detailed examples, which are provided for the purpose of illustration only and are not to be considered limiting of the invention unless otherwise specified.

EXAMPLES

Example 1: Solid Phase Integrin $\alpha_v\beta_3$ Ligand Binding Assay

This example sets forth a method to evaluate the ability of peptides of this invention to bind to integrin $\alpha_v\beta_3$ using a solid phase integrin $\alpha_v\beta_3$ ELISA assay, in which purified integrin $\alpha_v\beta_3$ is presented on the surface of microtiter wells in a native conformation. In this assay, the abilities of peptides in a concentration range extending from 1 µM to 0.5 nM to inhibit the binding of biotinylated extracellular matrix protein ligands, e.g. fibrinogen and vitronectin, to the integrin $\alpha_v\beta_3$ is readily evaluated. Bound ligand is detected with the use of a secondary reagent such as alkaline phosphatase conjugated streptavidin. Comparison of the activities of peptides can be achieved by identifying the concentration at which 50% of the ligand that can bind in the absence of an inhibitor is bound in the presence of the inhibitory peptide. This assay is used to estimate, in a non-physiological setting, the ability of a peptide to bind to $\alpha_v\beta_3$ and may indicate whether a given peptide could treat a disease state that involves the $\alpha_v\beta_3$ receptor.

Materials:

Immulon 2 microtiter plates

Integrin $\alpha_v\beta_3$, 500 µg/ml in phosphate buffered saline, pH 7.4, containing 0.1% NP40, 2 mM $CaCl_2$, 1 mM $MgCl_2$, 1 mM $MnCl_2$ (to be stored at −80° in single use, 5 µg aliquots)

Biotinylated fibrinogen (1 mg/ml) in phosphate buffered saline or biotinylated vitronectin.

Alkaline phosphatase conjugated streptavidin or alkaline phosphatase conjugated goat anti-biotin antibody (Sigma A7418)

Coating buffer: 20 mM Tris, pH 7.4, 150 mM NaCl, 2 mM $CaCl_2$, 1 mM $MgCl_2$, 1 mM $MnCl_2$ Blocking buffer: 50 mM Tris, pH 7.4, 100 mM NaCl, 2 mM $CaCl_2$, 1 mM $MgCl_2$, 1 mM $MnCl_2$, 3% Bovine serum albumin Binding buffer: 50 mM Tris, pH 7.4, 100 mM NaCl, 2 mM $CaCl_2$, 1 mM $MgCl_2$, 1 mM $MnCl_2$, 0.1% Bovine serum albumin 2-amino 2-methyl 1-propanol (PMP, JBL #1250B)

Phenolphthalein monophosphate (JBL Scientific, Inc. #1270D)

Alkaline phosphatase substrate buffer: 0.5M Tris, pH 10.2, 2% 2-amino 2-methyl 1-propanol, 0.1% $N_aN_3$, store in dark at room temperature Methods Preparation of ELISA plates:

1) Dilute 5 µg purified integrin $\alpha_v\beta_3$ into 10 ml of coating buffer to achieve a final concentration of 0.5 µg/ml. Aliquot 100 µl of the solution of diluted integrin per well of a 96 well Immulon II microtiter plate. Cover the plate and incubate overnight at +4° C.

2) Wash plate twice with binding buffer, 100 μl/well, per wash
3) Incubate plates with blocking buffer, 100 μl/well, for 3 h at room temperature
4) Wash blocked plates three times with binding buffer, 100 μl/well per wash
Use prepared plates immediately
Activity Assay
1) Dilute biotinylated fibrinogen in binding buffer to a final concentration of 4 μg/ml (6 nM)
2) Prepare serial twofold dilutions of peptide antagonist in binding buffer: 2, 1, 0.5, 0.25, 0.125, 0.067, 0.033, 0.016, 0.008, 0.004, 0.002 μM
3) Apply 50 μl of peptide antagonist and 50 μl of biotinylated fibrinogen and solutions to the wells of blocked VNR coated plates in triplicate; incubate at room temperature for three hours
4) Wash plate five times in binding buffer
5) Aliquot 100 μl of secondary reagent (diluted 1/2000 in binding buffer) per well of microtiter plate; incubate 1 hour at room temperature
6) Wash plate five times in binding buffer
7) Apply 100 μl of colorimetric reagent per well: Combine 0.3 g phenolphthalein monophosphate with 50 ml 2-amino 2-methyl 1-propanol buffer; incubate in the dark until color develops (20 to 60 minutes)
8) Stop color development with 150 μl of 30 mM Tris pH 8.0, 15 mM EDTA
9) Read plates at λ=560 nm For positive control: apply fibrinogen plus binding buffer, no inhibitor. For negative control: apply secondary reagent only. For inhibition control: apply 10 mM EDTA, final concentration, plus biotinylated fibrinogen.

Example 2: Cell Adhesion Assay

This example sets forth a method to evaluate the ability of a peptide of this invention to inhibit the ability of $\alpha_v\beta_3$-expressing melanoma cells to adhere to ligands.

In this assay, various concentrations of peptides are incubated with freshly resuspended cells from cell culture which are plated onto extracellular matrix proteins in the presence of the divalent cation co-factors required for integrin function. The IC50 or concentration of peptides required to inhibit 50% of the degree of adhesion exhibited by cells incubated on extracellular matrix proteins in the absence of inhibitors can be used to compare the effectiveness of inhibitory reagents. Wells of a Costar 48 non-tissue culture treated cluster plates (Costar #3547) are treated with 250 μl of a solution of 10 μg/ml human fibrinogen in phosphate buffered saline pH 7.4, for one hour at 37° C. The wells are rinsed with phosphate buffered saline (PBS). After rinsing, the wells are blocked with 250 μl of a 3% bovine serum albumin/PBS solution and incubated for one hour at, 37° C. Twofold or threefold serial dilutions of peptide antagonists in adhesion buffer (10 mM Hepes, pH 7.4, HBSS, 2 mM CaCl$_2$, 2 mM MgCl$_2$, 0.2 mM MnCl$_2$, 1% BSA) are prepared. Peptide concentration ranges are varied from 0.1 to 50 μM. Log phase growing M21 melanoma cells (which express high levels of the $\alpha_v\beta_3$ integrin) are resuspended by trypsinization. These cells are washed three times in an excess of warm adhesion buffer and resuspended at a final concentration of $4\times10^5$ cells/ml in adhesion buffer. 250 μl of peptide antagonist solutions and 250 μl of cell suspension (final of $2.5\times10^5$ cells) are aliquoted per well in triplicate wells and incubated at 37° C. for 20–30 minutes. Unbound cells are removed by aspiration. After the 30 minute incubation, the cells in each well are washed three to four times with warmed adhesion buffer to remove loosely adherent and nonadherent cells. The remaining cells in wells are fixed with 250 μl of 3.7% paraformaldehyde/phosphate buffered saline solution, pH 7.4, for 1 hour at room temperature. Fixative is removed and replaced with the same volume of 1% crystal violet in 10% methanol. The cells are stained for 1 hour at room temperature. After one hour of staining, the cells are washed in water until the dye is no longer washed from the cells. The cells were drained, air dried, extracted with 100 μl of 10% acetic acid, and read at 560 nm. The IC$_{50}$ peptide concentration is determined from the amount of peptide required to inhibit 50% of the binding exhibited by cells in the absence of peptide or other antagonists after background binding on BSA was subtracted. A desirable peptide is one with an activity of 20 μM or below.

Example 3: Cell Migration Assay

This example describes a method to evaluate the ability of peptide of this invention to inhinit cytokine-induced smooth muscle cell migration. Smooth muscle cell migration is a prerequisite for restenosis, and the assay identifies peptide inhibitors of this migratory process, and thus, potential inhibitors of restenosis. In this assay the number of cells that migrate in response to cytokine induction and the ability of various peptides to inhibit is easily measured. See also variations of this assay in Choi, E. T. et al., *J. Vasc. Surg.*, Vol. 19, pages 125–134 (1994).

Supplies:
Costar Transwell 8.0 μm (Catalog #3422) PDGF, bFGF or other chemoattractant
Vitronectin, fibrinogen or other extracellular matrix ligand BSA
Serum-free medium, supplemented only with insulin, antibiotics, 10 mM HEPES, pH 7.4, 2 mM CaCl$_2$, 2 mM MgCl2

Day 0: Passage cells 2:3 to obtain healthy, log-phase cultures.

Day 1: Dilute chemoattractant (PDGF, bFGF, etc., 1–10 ng/ml) and matrix protein (1–20 μg/ml) in insulin and antibiotic supplemented growth medium. Include controls for non-specific migration (0.5% BSA) and random migration (matrix protein in lower and upper chambers). Aliquot 500 μl into lower chamber, allow to equilibrate at 37° C., while preparing cells. This allows matrix protein to coat the lower surface.

Harvest cells: Wash monolayer with PBS or other saline solution. Treat with trypsin/EDTA, 5 ml/25 cm$^2$ of surface area for 5 min. Add BSA-containing migration buffer, triturate to obtain single cell suspension, count an aliquot in hemocytometer. Wash cells by centrifugation and resuspension to remove serum. Resuspend at $5\times10^5$ cells per ml in migration buffer plus inhibitors.

Add 100 μl to upper chamber. Incubate 37° C., 5% CO$_2$ for 6–18 hours, depending on cell type.

Day 2: Recover membrane insert. Remove cells from inner portion with Q-Tip cotton swab and place into a second tray containing 250 μl freshly prepared 1% crystal violet in 20% methanol, 80% water. Stain for 20 minutes.

Remove insert and wash thoroughly in water. Drain and dry the upper membrane surface with cotton swab. Oven dry until absolutely dry.

Extract the dye by placing dried insert into clean tray containing 250 μl 10% acetic acid. Extract for 5 minutes and agitate to ensure complete extraction. Discard membrane insert, recover an aliquot of dye extract and read at 500 nm.

Example 4: Screening Peptide Libraries Using Phage Display

This example provides a method for preparing peptide libraries that can be used for screening and optimizing peptides for a specific receptor generally in accordance with the method of Scott, J. K. and Smith, G. P. *Science*, 249: 386–390 (1990). A phage display library comprises tens to hundreds of millions of variable amino acid sequences that are displayed on the surface of a bacteriophage virion. Generally, two viral proteins have been used to display peptides, a minor coat protein pIII and the major coat protein pVIII. Both proteins are synthesized with short signal sequences that allow them to be transported to the bacterial inner membrane, where they are cleaved by signal peptidase to form mature proteins. The mature proteins are added to the viral coat as it assembles in and emerges from the inner membrane. The major coat protein, pVIII, forms the body of the phage, whereas four or five copies of the minor coat protein, pIII, are added at the trailing end of the merging virion. In both coat proteins, the peptide is inserted at or within a few residues of the amino terminus of the mature protein.

To make a phage library, a degenerate oligonucleotide is synthesized using single nucleotides at positions encoding the invariant amino acids and variable nucleotides at positions encoding variable amino acids. For example, all 20 amino acids may be represented by NNX where N represents the equimolar amounts of the four nucleotides and X can either be equimolar amounts of G and T or equimolar amounts of G and C. The appropriate ends for ligation with the vector can then be generated by restriction endonuclease digestion. After the ligated product is introduced into bacterial cells by electroporation, the phage are propagated, collected, and purified. Very large libraries of up to 200–300 million independent clones have been constructed using the phage method.

Synthesis of Oligonucleotides

All oligonucleotides were synthesized on an Applied Biosystems Model 394 DNA/RNA synthesizer (Applied Biosystems, Foster city, Calif.) using standard phosphoramidate chemistry. Controlled pore glass (CPG) beads were used as the synthesis support for oligonucleotides for standard mutagenesis and polystyrene beads (ABI) for oligonucleotides for library construction.

The synthesis of N-terminal oligonucleotides was started by packing 1.0 µmol of dimethoxytrityl derivatized deoxyribonucleotide polystyrene beads into each of ten separate 1.0 µmol synthesis columns. Since the synthesis proceeds in the 3' to 5' direction, the 3' complementary end and the first random triplet were initially synthesized on the columns. Following this, the ten columns were opened and the beads were emptied into a vessel and 2 ml of acetonitrile was added. The suspension was mixed by pipetting up and down and 200 µl was aliquotted into ten new columns. After capping the columns, the next triplet was synthesized. The columns were once again opened, mixed and divided into ten new columns. This was repeated ten times for the randomized libraries and nine times for the cysteine enriched libraries as well as for the non-RGD library. After synthesis of the last random triplet, the beads were again mixed into 2 ml acetonitrile and the suspension was equally divided into forty individual columns by pipetting fifty µl into each. The 5' ends of the oligonucleotides were synthesized in the same fashion but using different sequences. The forty N- and forty C- terminal oligonucleotides were purified by OPC columns (ABI) or by denaturing gel electrophoresis.

Four libraries were constructed which were enriched in cysteine residues and excluded a carboxyl terminal glycine after arginine. Separate columns were now included for glycine and arginine and an extra column was included for cysteine. Since cysteine was encoded by the same triplet combination as arginine in the fully random synthesis and tryptophan on the glycine column, cysteine was now combined with tryptophan. This synthesis was performed using 0.2 µmol of the polystyrene beads per column except for the glycine and arginine columns which received 0.1 µmol beads. Following the synthesis of the 3' complimentary end and the first triplet, columns 2–12, were opened and the resins mixed into 2.1 ml acetonitrile. One hundred µl was added into a new column number 1 for the synthesis of a triplet coding for arginine and 200 µl was aliquotted. This procedure was repeated nine times as described above and the 5' ends of the oligonucleotides were then added. Two oligonucleotides were synthesized to make libraries with a cysteine as residue 10 and two with an alanine as the tenth residue. The carboxyl terminal oligonucleotide was essentially made in a similar way, except that the mixing order for columns 1 and 2 was reversed. This is because the carboxyl terminal oligonucleotide is the reverse complement of the amino terminal. Thus, after the mixing of columns 1 and 3–12, one hundred µl was packed into a new column number 1 for the synthesis of a triplet coding for arginine. Column number 2 was then added to the remaining suspension as for the amino terminal oligonucleotide.

Vectors

The vectors were constructed by sequential stepwise oligonucleotide-directed in vitro mutagenesis (Kunkel, 1987). Both the N-terminal, ED07 and the C-terminal, IX47 vectors were derived from the previously described ED03 and IX421 vectors. They are originally engineered from M13 mp19 (Yanisch-Perron et al., 1985) and contain all necessary elements for the normal growth of this filamentous phage.

ED07 which is used for the construction of the N-terminal half of the peptide libraries is essentially similar to ED03 except that the FokI site at position 3547 was eliminated. BsaI sites at positions 6366 and 6866 were introduced as well as two EcoRI sites at positions 6386 and 6852.

IX47 was constructed from IX40 which is a precursor of IX421. IX40 is identical to IX421 except for a change in the FokI overhang at position 3547 (TTTT rather than CTTC) and a T rather than a C at position 4492. These differences have no relevance in the present work and are mentioned here only for the completeness of vector description. A XbaI and a XhoI site were introduced into IX40 at positions 5877 and 6748, respectively. The vector was cut with these enzymes and the larger fragment was saved. Next, XhoI and XbaI sites were introduced into the original IX40 at positions 5876 and 6744, respectively. Restriction digestion with these enzymes released a 868 nucleotide long fragment which was ligated into the complementary ends of the large fragment. This construct was saved as the C-terminal vector IX47.

Construction of Peptide Libraries

The libraries are built in two steps. In the first step, separate N- and C-terminal libraries (sub-libraries) are made which are subsequently joined into the combinatorial library. Uracil containing single-stranded ED07 and IX47 DNA was isolated. To obtain enough material, two identical mutagenesis reactions were then performed to introduce the random oligonucleotides into each vector. Each reaction contained 2.5 pmol uracil DNA, 125 pmol oligonucleotide (molar ratio of template oligo is 1:5), 20 mM Tris-HCL, pH 7.4, 2 mM MgCl, and 50 mM NaCl in a total volume of 50 µl. The reactions were heated to 75° C. for 2 minutes and cooled to room temperature over a 40 minute period for annealing of the oligonucleotides to the vector. After annealing, the reactions were transferred to ice and 15 µl of a buffer containing 5 mM of each dATP, dCTP, dGTP, and dTTP, 10 mM ATP, 100 mM Tris-HCL, pH 7.4, 50 mM MgCl$_2$, 20 mM DTT, 5 U T7 DNA polymerase and 20 U T4 DNA ligase was added. The reactions were kept on ice for 5 minutes followed by incubation at room temperature for 5 minutes and 37° C. for 1 hour. The two identical reactions were pooled, extracted with phenol/CHCl$_3$, precipitated with ethanol and resuspended in 21 µl of TE pH 8.0. Multiple electroporations were performed into DH10B cells to obtain at least $10^8$ transformants in each sub-library. Usually 4 transformations, each with 2 µl of the mutagenesis reaction was enough to give the required number of clones. Each set of electroporations was added into 6 ml of 2× YT media and incubated while shaking at 37° C. for 8 hours. The phage containing supernatant was saved as the amplified sub-library.

In the second step of the library construction, RF DNA from each sub-library was prepared. One hundred µg of each sub-library DNA was cut to completion with BsaI, extracted with phenol/CHCl$_3$ and resuspended in 100 µl of TE pH 7.4. The digestion of both the N- and C-terminal plasmids gives rise to one large (approximately 6.5 kb) and one small (approximately 0.5 kb) fragment. The N-terminal large fragment is ligated with the C-terminal small fragment to generate the combinatorial library. The desired fragments were isolated on a Gen-Pak FAX (Waters) HPLC column at 30° C. The sample (100 µl) was injected onto a column equilibrated with 60% buffer A (25 mM Tris-HCl, pH 8.0, 1 mM EDTA) and 40% buffer B (25 mM Tris-HCL, pH 8.0, 1 mM EDTA, 1M NaCl) using a flow rate of 0.5 ml/min. A linear gradient of 40% buffer A, 60% buffer B was run over 40 minutes. In this system, the smaller fragment eluted after approximately 30 minutes followed by the larger piece at about 40 minutes. Fractions containing the large fragment (6.5 kb) from the N-terminal library and the small fragment from the C-terminal library were collected and pooled. Both fragments were recovered by centrifugation after the addition of an equal volume of isopropanol and keeping them on ice for 30 minutes. This procedure eliminated the co-precipitation of NaCl with the DNA. Each fragment was resuspended in 50 µl TE pH 7.4.

Three ligation reactions were set up, each containing 10 µl of both the large and small fragment, 20 mM Tris-HCL pH 7.6, 5 mM MgCl$_2$, 0.5 mM DTT and 1 mM ATP in a final volumn of 400 µl. Ligations were carried out at 15° C. for at least 16 hours. The three ligations were pooled, extracted with phenol/CHCl$_3$ and precipitated twice with ethanol before resuspension in 30 µl TE pH 8.0. Multiple electrotransformations were performed to obtain at least 1×10$^9$ primary transformants. Usually, ten transformations, each with 2 µl DNA and 35 µl competent cells were enough to generate the desired amount of transformants. The library was then amplified using standard protocols.

Preparation of Electrocompetent Cells

Electrocompetent XL-1 Blue, DH10B, or MC 1061 cells were prepared by inoculating 500 ml 2× YT media in a 2 liter baffle flask with several loopfulls of bacterial colonies that were grown overnight on LB plates. The culture was incubated at 37° C. in an orbital shaker until late log phase. The culture was chilled on wet ice and the bacteria were pelleted at 5000 xg for 15 minutes at 4° C. The pellet was resuspended in 500 ml ice cold deionized water and centrifuged again. The previous step was repeated once using 250 ml water. The pellet was then resuspended in 100 ml 10% glycerol in water and centrifuged. The final pellet was resuspended in 1–2 ml residual supernatant, frozen in aliquots in an ethanol/dry ice bath and stored a −80° C. Care was taken throughout the procedure to keep the bacteria at 4° C.

Isolation of the Replicative Form of M13 Phage

Five ml of overnight XL-1 Blue cells were added to 500 ml 2× YT media. After incubation for 1.5 hour, 10 µl of a high titer phage stock ($10^{11}$ pfu/ml) were added and the culture was incubated for an additional 6 hours. Bacteria were harvested by centrifugation and washed once to decrease contamination of the plasmid with single-stranded phage DNA. The cells were resuspended in 20 ml 10 mM EDTA, pH 8.0 and 40 ml 0.2M NaOH, 1% SDS was added. After 10 minutes on ice, 20 ml of 5M potassium acetate was added. The mixture was shaken and incubated on ice for 5 minutes. After centrifugation at 7000 xg for 15 minutes, the supernatant was filtered through a single layer of a Kimwipe tissue and an equal volume of isopropanol was added to precipitate the nucleic acids. The pellet was resuspended in 10 ml of 10 mM Tris-HCl, 1 mM EDTA, pH 8.0 and 50 µl of 10 mg/ml RNase A was added. After incubation for 15 minutes at 37° C., the mixture was extracted with phenol/CHCl$_3$ and precipitated with ethanol. The pellet was resuspended in 2 ml of 10 mM Tris-HCL, 1 mM EDTA pH 8.0, and the plasmid DNA was precipitated with polyethylene glycol before final purification by centrifugation on a CsCl/EtBr gradient.

Vectors

The N-terminal (EDj03) and C-terminal (IX421) peptide library vectors were constructed by stepwise sequential oligonucleotide-directed in vitro mutagenesis. Both vectors are derived from M13 mp19.

EDj03 was constructed in short as follows: A pseudo-wild type gene VIII sequence was synthesized by annealing overlapping oligonucleotides. The oligonucleotides were phosphorylated and heated to 65° C. After slow cooling to room temperature the annealed product was ligated into dephosphorylated M13 mp19 cut with EcoRI and HindIII. These restriction sites were subsequently destroyed in the final vector construct by mutagenesis. The lac Z gene was deleted and FokI restriction enzyme sites at positions 239 and 7244 were removed. The FokI overhang at position 3561 was changed from TTTT to CTTC. Overlapping oligonucleotides were used to construct a phosphorylase A leader sequence, in which amino acid at position 19, coding for alanine, was changed to encode threonine. This sequence was inserted between the lac promoter/operator and pseudo-gene VIII. Finally, 33 nucleotides encoding the sequence (SEQ ID:19) YGGFMLLRHPG, was inserted between the leader sequence and pseudo gene VIII. All nucleotide changes within coding sequences of the phage genome were made without changing the coding information.

The vector IX421 was constructed by first synthesizing the pseudo gene VIII sequence with BamHI and HindIII ends. It was then ligated into M13 mp19, cut with the same enzymes, and dephosphorylated. The lac Z gene was deleted and FokI sites at positions 239 and 7244 were removed and the FokI overhang at nucleotide 3561 was changed from TTTT to CTTC in analogy with the construction of EDj03. A FokI site was introduced at position 6223.

Example 5: ELISA-Based Phage Binding Assay

The ability of various peptide-expressing phage to bind to $\alpha_v\beta_3$ was evaluated using an ELISA-based assay. Immulon 2 plates were coated overnight at 4° C. with 1 µg/ml $\alpha_v\beta_3$ in coupling buffer (150 mM NaCl, 20 mM Tris ph 7.4, 1 mM CaCl$_2$, 1 mM MgCl$_2$, 1 mM MnCl$_2$, 0.02% NaN$_3$). Plates were blocked for 2 hr with binding buffer 100 mM NaCl, 50 mM NACl, 50 mM Tris ph 7.4, 2 mM CaCl$_2$, 1 mM MgCl$_2$, 1 mM MnCl$_2$, 0.02% NaN$_3$, 1 mg/ml BSA (0.1% BSA)) lacking BSA, but containing 5% nonfat dried milk instead. Plates were then washed 3 times with binding buffer to remove any residual nonfat dried milk before the addition of any phage. High titer peptide-expressing phage in Luria Broth supernatants, or PEG precipitated purified phage resuspended in binding buffer, were then added to plates and incubated for 1 hr at room temperature. Bound phage were detected by inhibiting for 1 hr at room temperature (100 mg/ml in binding buffer) a biotinylated rabbit anti-M13 antibody followed by a strepavidin alkaline phosphatase conjugate (1:4000 dilution in binding buffer). Alkaline phosphatase activity was determined using phenolphthalein monophosphate (PMP) as a substrate and absorbances measured at 560 mM. Between the addition of each reagent, plates were washed a total of 6 times with binding buffer.

All publications and patent applications mentioned in this specification are herein incorporated by reference to the same extent as if each individual publication or patent application was specifically and individually indicated to be incorporated by reference.

The invention now being fully described, it will be apparent to one of oridinary skill in the art that many changes and modifications can be made thereto without departing from the spirit or scope of the appended claims.

A listing of the amino acid sequences for the peptides disclosed herein is presented in the following Sequence Listing.

The subject matter claimed is:

1. A non-RGD cyclic peptide that is capable of binding to the $\alpha_v\beta_3$ integrin receptor represented by the formula:

(SEQ 10:2)

Arg—Cys—$X_i$—Gly—Asp—$X_{i+3}$—$X_{i+4}$—Cys—$X_{i+6}$ wherein $X_i$ is selected from the group consisting of Gly, Ser, and Ala, $X_{i+3}$ is Ser, $X_{i+4}$, and $X_{i+6}$ are any amino acid.

2. The peptide of claim 1 wherein Xi+3 is Ser.

3. The peptide of claim 1 represented by the formula (SEQ 10:20)

Arg—Cys—$X_i$—Gly—Asp—Ser—Met—Cys—Thr.

4. The peptide of claim 3 wherein $X_i$ is Gly.

5. The peptide of claim 3 wherein $X_i$ is Ser.

6. The peptide of claim 3 wherein $X_i$ is Ala.

7. A pharmaceutical composition comprising the non-RGD cyclic peptide of claim 1 and a pharmaceutically acceptable carrier.

8. The pharmaceutical composition as in claim 7 wherein the non-RGD cyclic peptide has the sequence, (SEQ ID:13) Arg-Cys-Gly-Gly-Asp-Ser-Met-Cys-Tyr.

9. The pharmaceutical composition as in claim 7 wherein the non-RGD cyclic peptide has the sequence, (SEQ ID:14) Arg-Cys-Ser-Gly-Asp-Ser-Met-Cys-Tyr.

10. The pharmaceutical composition as in claim 7 wherein the non-RGD cyclic peptide has the sequence, (SEQ ID:15) Arg-Cys-Ala-Gly-Asp-Ser-Met-Cys-Tyr.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 2
        ( D ) OTHER INFORMATION: /note= "Xaa is penicillamine."

( x i ) SEQUENCE DESCRIPTION: SEQ ID NO:1:

```
Gly  Xaa  Gly  Arg  Gly  Asp  Ser  Pro  Cys  Ala
1                  5                        10
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Disulfide bond
        ( B ) LOCATION: 2..8

( i x ) FEATURE:
        ( A ) NAME/KEY: Region
        ( B ) LOCATION: 3
        ( D ) OTHER INFORMATION: /note= "Xaa is Gly, Ala or Ser."

( i x ) FEATURE:
        ( A ) NAME/KEY: Region
        ( B ) LOCATION: one-of(6, 7, 9)
        ( D ) OTHER INFORMATION: /note= "Xaa is any amino acid."

( x i ) SEQUENCE DESCRIPTION: SEQ ID NO:2:

```
Arg  Cys  Xaa  Gly  Asp  Xaa  Xaa  Cys  Xaa
1                  5
```

( 2 ) INFORMATION FOR SEQ ID NO:3:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Disulfide bond
  ( B ) LOCATION: 2..8

( i x ) FEATURE:
  ( A ) NAME/KEY: Region
  ( B ) LOCATION: one-of(7, 9)
  ( D ) OTHER INFORMATION: /note= "Xaa is any amino acid."

( x i ) SEQUENCE DESCRIPTION: SEQ ID NO:3:

Arg Cys Gly Gly Asp Ser Xaa Cys Xaa
1                   5

( 2 ) INFORMATION FOR SEQ ID NO:4:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Disulfide bond
    ( B ) LOCATION: 2..8

( i x ) FEATURE:
    ( A ) NAME/KEY: Region
    ( B ) LOCATION: one-of(7, 9)
    ( D ) OTHER INFORMATION: /note= "Xaa is any amino acid."

( x i ) SEQUENCE DESCRIPTION: SEQ ID NO:4:

Arg Cys Ala Gly Asp Ser Xaa Cys Xaa
1                   5

( 2 ) INFORMATION FOR SEQ ID NO:5:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Disulfide bond
    ( B ) LOCATION: 2..8

( i x ) FEATURE:
    ( A ) NAME/KEY: Region
    ( B ) LOCATION: one-of(7, 9)
    ( D ) OTHER INFORMATION: /note= "Xaa is any amino acid."

( x i ) SEQUENCE DESCRIPTION: SEQ ID NO:5:

Arg Cys Gly Gly Asp Asn Xaa Cys Xaa
1                   5

( 2 ) INFORMATION FOR SEQ ID NO:6:

( i ) SEQUENCE CHARACTERISTICS:
    ( A ) LENGTH: 9 amino acids
    ( B ) TYPE: amino acid
    ( C ) STRANDEDNESS: single (D) TOPOLOGY: linear (ii) MOLECULE TYPE: peptide (ix) FEATURE:
    (A) NAME/KEY: Disulfide bond
    (B) LOCATION: 2..8

(ix) FEATURE:
    (A) NAME/KEY: Region
    (B) LOCATION: one-of(7, 9)
    (D) OTHER INFORMATION: /note= "Xaa is any amino acid."

(xi) SEQUENCE DESCRIPTION: SEQ ID NO:6:

Arg Cys Ala Gly Asp Asn Xaa Cys Xaa
1               5

(2) INFORMATION FOR SEQ ID NO:7:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
    (A) NAME/KEY: Disulfide bond
    (B) LOCATION: 2..8

(ix) FEATURE:
    (A) NAME/KEY: Region
    (B) LOCATION: one-of(7, 9)
    (D) OTHER INFORMATION: /note= "Xaa is any amino acid."

(xi) SEQUENCE DESCRIPTION: SEQ ID NO:7:

Arg Cys Gly Gly Asp Tyr Xaa Cys Xaa
1               5

(2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
    (A) NAME/KEY: Disulfide bond
    (B) LOCATION: 2..8

(ix) FEATURE:
    (A) NAME/KEY: Region
    (B) LOCATION: one-of(7, 9)
    (D) OTHER INFORMATION: /note= "Xaa is any amino acid."

(xi) SEQUENCE DESCRIPTION: SEQ ID NO:8:

Arg Cys Ala Gly Asp Tyr Xaa Cys Xaa
1               5

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:

(A) NAME/KEY: Disulfide bond
            (B) LOCATION: 2..8

(ix) FEATURE:
            (A) NAME/KEY: Region
            (B) LOCATION: one-of(7, 9)
            (D) OTHER INFORMATION: /note= "Xaa is any amino acid."

(xi) SEQUENCE DESCRIPTION: SEQ ID NO:9:

Arg  Cys  Gly  Gly  Asp  Thr  Xaa  Cys  Xaa
    1                        5

(2) INFORMATION FOR SEQ ID NO:10:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Disulfide bond
            (B) LOCATION: 2..8

(ix) FEATURE:
            (A) NAME/KEY: Region
            (B) LOCATION: one-of(7, 9)
            (D) OTHER INFORMATION: /note= "Xaa is any amino acid."

(xi) SEQUENCE DESCRIPTION: SEQ ID NO:10:

Arg  Cys  Ala  Gly  Asp  Thr  Xaa  Cys  Xaa
    1                        5

(2) INFORMATION FOR SEQ ID NO:11:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Disulfide bond
            (B) LOCATION: 2..8

(ix) FEATURE:
            (A) NAME/KEY: Region
            (B) LOCATION: one-of(7, 9)
            (D) OTHER INFORMATION: /note= "Xaa is any amino acid."

(xi) SEQUENCE DESCRIPTION: SEQ ID NO:11:

Arg  Cys  Gly  Gly  Asp  Asp  Xaa  Cys  Xaa
    1                        5

(2) INFORMATION FOR SEQ ID NO:12:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Disulfide bond
            (B) LOCATION: 2..8

(ix) FEATURE:
            (A) NAME/KEY: Region (B) LOCATION: one-of(7, 9)
            (D) OTHER INFORMATION: /note= "Xaa is any amino acid."

(x i) SEQUENCE DESCRIPTION: SEQ ID NO:12:

Arg  Cys  Ala  Gly  Asp  Asp  Xaa  Cys  Xaa
    1                    5

(2) INFORMATION FOR SEQ ID NO:13:

(i) SEQUENCE CHARACTERISTICS:
            (A) LENGTH: 9 amino acids
            (B) TYPE: amino acid
            (C) STRANDEDNESS: single
            (D) TOPOLOGY: linear (i i) MOLECULE TYPE: peptide (i x) FEATURE:
            (A) NAME/KEY: Disulfide bond
            (B) LOCATION: 2..8

(x i) SEQUENCE DESCRIPTION: SEQ ID NO:13:

Arg  Cys  Gly  Gly  Asp  Ser  Met  Cys  Tyr
    1                    5

(2) INFORMATION FOR SEQ ID NO:14:

(i) SEQUENCE CHARACTERISTICS:
            (A) LENGTH: 9 amino acids
            (B) TYPE: amino acid
            (C) STRANDEDNESS: single
            (D) TOPOLOGY: linear (i i) MOLECULE TYPE: peptide (i x) FEATURE:
            (A) NAME/KEY: Disulfide bond
            (B) LOCATION: 2..8

(x i) SEQUENCE DESCRIPTION: SEQ ID NO:14:

Arg  Cys  Ser  Gly  Asp  Ser  Met  Cys  Tyr
    1                    5

(2) INFORMATION FOR SEQ ID NO:15:

(i) SEQUENCE CHARACTERISTICS:
            (A) LENGTH: 9 amino acids
            (B) TYPE: amino acid
            (C) STRANDEDNESS: single
            (D) TOPOLOGY: linear (i i) MOLECULE TYPE: peptide (i x) FEATURE:
            (A) NAME/KEY: Disulfide bond
            (B) LOCATION: 2..8

(x i) SEQUENCE DESCRIPTION: SEQ ID NO:15:

Arg  Cys  Ala  Gly  Asp  Ser  Met  Cys  Tyr
    1                    5

(2) INFORMATION FOR SEQ ID NO:16:

(i) SEQUENCE CHARACTERISTICS:
            (A) LENGTH: 6 amino acids
            (B) TYPE: amino acid
            (C) STRANDEDNESS: single
            (D) TOPOLOGY: linear (i i) MOLECULE TYPE: peptide (x i) SEQUENCE DESCRIPTION: SEQ ID NO:16:

```
        Gly Arg Gly Asp Ser Pro
        1               5
```

( 2 ) INFORMATION FOR SEQ ID NO:17:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
        Ala Cys Pro Ser Arg Leu Asp Ser Pro Cys Gly
        1               5                   10
```

( 2 ) INFORMATION FOR SEQ ID NO:18:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
        Gly Arg Gly Asp Ser
        1               5
```

( 2 ) INFORMATION FOR SEQ ID NO:19:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
        Tyr Gly Gly Phe Met Leu Leu Arg His Pro Gly
        1               5                   10
```

( 2 ) INFORMATION FOR SEQ ID NO:20:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Disulfide bond
        ( B ) LOCATION: 2..8

( i x ) FEATURE:
        ( A ) NAME/KEY: Region
        ( B ) LOCATION: 3
        ( D ) OTHER INFORMATION: /note= "Xaa is Gly, Ser or Ala."

( x i ) SEQUENCE DESCRIPTION: SEQ ID NO:20:

```
        Arg Cys Xaa Gly Asp Ser Met Cys Thr
        1               5
```